(12) United States Patent
Nagano et al.

(10) Patent No.: US 8,931,712 B2
(45) Date of Patent: Jan. 13, 2015

(54) FRAGRANCE DEVICE FOR VEHICLE AND SEALING COMPONENT USED THEREIN

(75) Inventors: Hideki Nagano, Saitama (JP); Hisayoshi Yoshizaki, Saitama (JP); Toshio Tsubakida, Saitama (JP); Shinichi Hara, Saitama (JP); Yoshie Mizuno, Saitama (JP); Naoto Hayashi, Saitama (JP)

(73) Assignee: Valeo Japan Co., Ltd., Saitama (JP)

( * ) Notice: Subject to any disclaimer, the term of this patent is extended or adjusted under 35 U.S.C. 154(b) by 775 days.

(21) Appl. No.: 13/148,258

(22) PCT Filed: Jan. 29, 2010

(86) PCT No.: PCT/JP2010/051251
§ 371 (c)(1),
(2), (4) Date: Aug. 5, 2011

(87) PCT Pub. No.: WO2010/090141
PCT Pub. Date: Aug. 12, 2010

(65) Prior Publication Data
US 2011/0290903 A1    Dec. 1, 2011

(30) Foreign Application Priority Data

Feb. 5, 2009  (JP) .................... 2009-025394
Feb. 5, 2009  (JP) .................... 2009-025396
May 28, 2009  (JP) .................... 2009-128809

(51) Int. Cl.
*A61L 9/04*        (2006.01)
*A62C 13/62*       (2006.01)
(Continued)

(52) U.S. Cl.
CPC ............... *B60H 3/0007* (2013.01); *A61L 9/12* (2013.01); *A61L 9/122* (2013.01); *A61L 9/125* (2013.01); *A61L 2209/16* (2013.01)
USPC ............ 239/34; 239/302; 239/444; 239/569; 165/41; 165/202; 62/244

(58) Field of Classification Search
USPC ......... 239/34, 47, 57, 99, 302, 310, 311, 443, 239/444, 446, 569, 581.1; 165/41, 42, 43, 165/202, 203, 204; 62/239, 244
See application file for complete search history.

(56) References Cited

U.S. PATENT DOCUMENTS 5,042,567 A * 8/1991 Kajimoto et al. ............... 165/42
6,904,763 B2 * 6/2005 Araki et al. ..................... 62/244
(Continued)

FOREIGN PATENT DOCUMENTS

JP        6343841        3/1988
JP        2225125 A      9/1990
(Continued)

OTHER PUBLICATIONS

English language abstract for JP 2225125 extracted from the espacenet.com database on Aug. 11, 2011, 13 pages.
(Continued)

*Primary Examiner* — Justin Jonaitis
(74) *Attorney, Agent, or Firm* — Howard & Howard Attorneys PLLC

(57) ABSTRACT

The present invention provides a fragrance device for a vehicle capable of supplying plural fragrant ingredients to the inside of the vehicle as being contained in air flow of a vehicle-use air-conditioning device with a simple structure. The fragrance device for a vehicle according to the present invention includes a main body 10 having a fragrance retention container 5, an inlet passage 6, an outlet passage 7, an inlet passage opening/closing door 8 and an outlet passage opening/closing door 9, an actuator 11 fixed to the main body 10, and a cam 14 which rotationally drives a rotary shaft 12 of the inlet passage opening/closing door and a rotary shaft 12 of the outlet passage opening/closing door.

23 Claims, 21 Drawing Sheets

(51) Int. Cl.
*A62C 13/66* (2006.01)
*A62C 35/58* (2006.01)
*B60H 3/00* (2006.01)
*A61L 9/12* (2006.01)

(56) References Cited

U.S. PATENT DOCUMENTS 7,096,924 B2 * 8/2006 Araki et al. .................. 165/41
2002/0153132 A1 * 10/2002 Nagano .......................... 165/202

FOREIGN PATENT DOCUMENTS

| | | |
|---|---|---|
| JP | 06127264 | 5/1994 |
| JP | 06-270664 A | 9/1994 |
| JP | 10297247 | 11/1998 |
| JP | 11278048 | 10/1999 |
| JP | H11-348530 A | 12/1999 |
| JP | 3211410 B2 | 9/2001 |
| JP | 2003237364 | 8/2003 |
| JP | 2003275290 | 9/2003 |
| JP | 3211410 B2 | 9/2011 |

OTHER PUBLICATIONS

English language abstract and translation for JP 06127264 extracted from the PAJ database on Aug. 11, 2011, 31 pages.
English language abstract and translation for JP 10297247 extracted from the PAJ database on Aug. 11, 2011, 22 pages.
English language abstract and translation for JP 11278048 extracted from the PAJ database on Aug. 11, 2011, 33 pages.
English language translation for JP S63-43841, 4 pages.
English language abstract and translation for JP 2003237364 extracted from the PAJ database on Aug. 11, 2011, 39 pages.
English language abstract and translation for JP 2003275290 extracted from the PAJ database on Aug. 11, 2011, 22 pages.
International Search Report for Application No. PCT/JP2010/051251 dated Feb. 19, 2010, 4 pages.
English language abstract and machine-assisted English translation for JP H11-348530 extracted from the PAJ database on Mar. 17, 2014, 27 pages.
English language abstract and machine-assisted English translation for JP 06-270664 extracted from the espacenet.com database on Jun. 6, 2013, 23 pages.
JP 3211410 English language abstract extracted from espacenet.com Sep. 8, 2011, 1 page and English language translation for JP 3211410 extracted from the PAJ database on Sep. 8, 2011, 24 pages.
English language abstract not available for JP 3211410. However, see English language translation extracted from the PAJ database on Sep. 8, 2011, 25 pages.

* cited by examiner

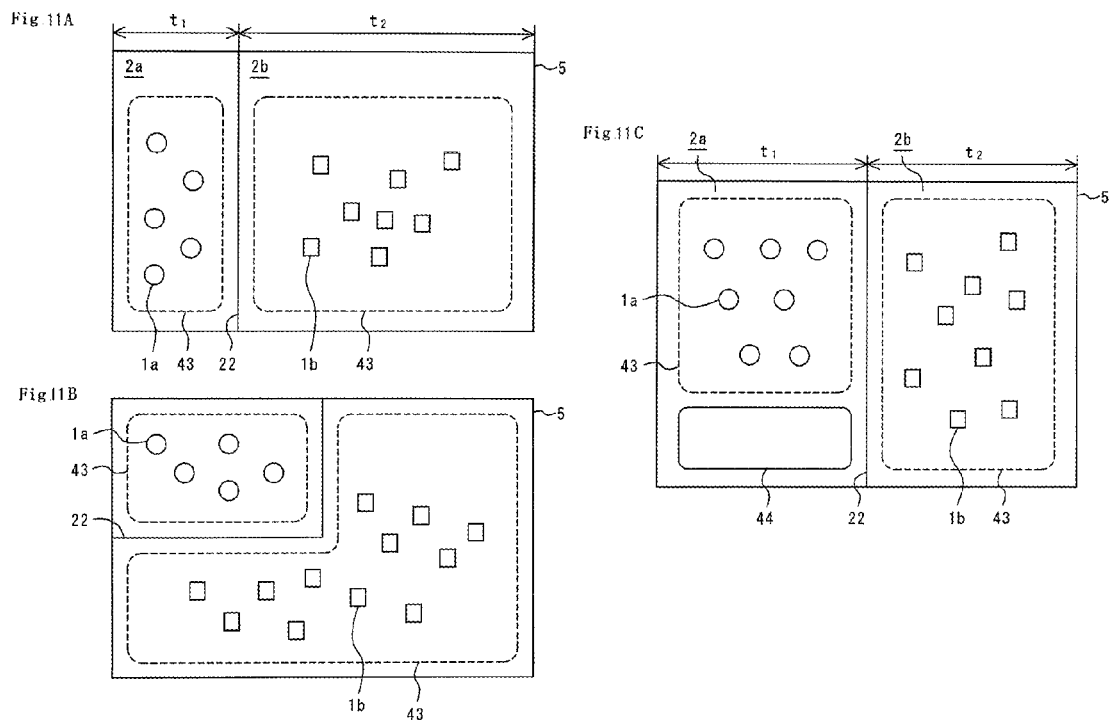

2b 3b 3a 1b 1a 43 43 4a 4b

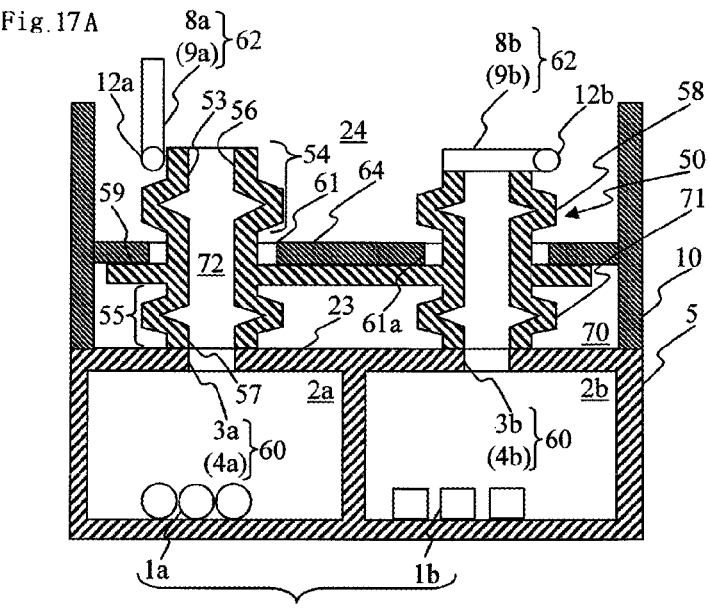
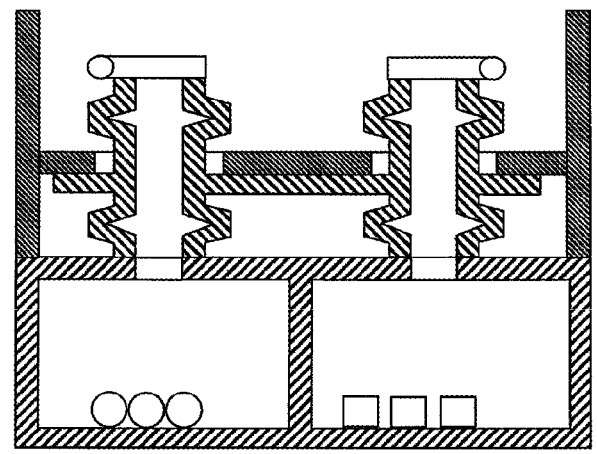
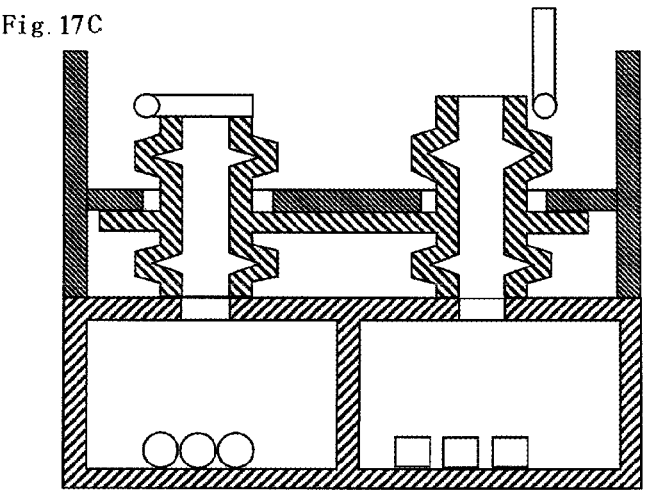

FRAGRANCE DEVICE FOR VEHICLE AND SEALING COMPONENT USED THEREIN

RELATED APPLICATIONS

This application claims priority to and all the advantages of International Patent Application No. PCT/JP2010/051251, filed on Jan. 29, 2010, which claims priority to Japanese Patent Application No. JP2009-025394, filed on Feb. 5, 2009, Japanese Patent Application No. JP2009-025396, filed on Feb. 5, 2009, and Japanese Patent Application No. JP2009-128809, filed on May 28, 2009.

TECHNICAL FIELD

The present invention relates to a fragrance device for a vehicle capable of supplying a fragrant ingredient of a fragrant agent accommodated in a fragrance retention container to the inside of the vehicle as being contained in air flow of an air-conditioning device for the vehicle. Further, the present invention relates to a sealing component used for the fragrance device for a vehicle.

BACKGROUND ART

With a fragrance device in the related art wafting a comfortable aroma in a room by utilizing a fragrant ingredient of a fragrant agent, aroma sensitivity of humans tends to be decreased after specific time passes even when aroma concentration is high in the case that a fragrant ingredient is naturally supplied into a room. Accordingly, there has been proposed a fragrance device capable of maintaining a comfortable aroma space for a long time by controlling supplying time of the fragrant ingredient intermittently. However, the above fragrance device is to perform uniform control without performing control corresponding to characteristics of fragrant ingredients even in a case of using several kinds of fragrant ingredients having different aroma. When a fragrant ingredient having a different usage purpose is used, there is a case that it is not necessarily desirable to maintain the aroma space for a long time. For example, when a user selects a fragrant ingredient having a relaxation effect, decrease in power of concentration is caused by maintaining the aroma space having the relaxation effect for a long time. Accordingly, it is not appropriate to continue supplying aroma having a relaxation effect during vehicle driving in view of ensuring safety driving of a vehicle.

In order to prevent decrease in power of concentration while suppressing decrease of an awakening level due to supply of relax-type fragrant ingredient, there has been disclosed a fragrance device including supply means which respectively supplies a refresh-type fragrant ingredient having a refreshment effect to increase the awakening level of consciousness and a relax-type fragrant ingredient having a relaxation effect to decrease the awakening level of consciousness, a refreshment selecting switch for selecting to supply the refresh-type fragrant ingredient by a user, a relaxation selecting switch for selecting to supply the relax-type fragrant ingredient by the user, and control means to control the supply means to repeatedly perform a supply pattern to supply the refresh-type fragrant ingredient when supplying of the refresh-type fragrant ingredient is selected by the refreshment selecting switch and to supply the refresh-type fragrant ingredient for predetermined times after supplying the relax-type fragrant ingredient for predetermined times when supplying of the relax-type fragrant ingredient is selected by the relaxation selecting switch (for example, see Patent document 1).

Further, there has been disclosed an inexpensive fragrance device regarding specific shapes of a fragrance device for a vehicle (for example, see Patent document 2). In the above fragrance device, a single actuator performs opening/closing of plural cartridges and a support plate supports the actuator, the cartridges, and adjusting parts to open/close outlet passage of fragrant ingredients. Opening/closing of the passage is performed by rotating the adjusting parts sandwiched between the support plate and the cartridges to predetermined positions. The actuator is inexpensive as being single and the device is compact as the respective parts being aggregated on the support plate.

Further, there has been disclosed a fragrance device as a device to supply fragrant ingredients to the inside of a vehicle as holding plural fragrant ingredients at a fragrance retention container and controlling air flow passing through the inside of the fragrance retention container by opening/closing electromagnetic valves disposed at passages located at the upstream and downstream of the fragrance retention container (for example, see Patent document 3). In order to control a fragrant ingredient to be supplied to the inside of a vehicle, the fragrance device adjusts the amount of the fragrant ingredient to be supplied with opening frequency and opening degree of the fragrance retention container and rotational strength of a blower.

CITED DOCUMENT

Patent Document

Patent document 1: Japanese Patent No. 3211410
Patent document 2: Japanese Patent Application Laid-open No. 2003-237364
Patent document 3: Japanese Patent Application Laid-open No. 11-278048

DISCLOSURE OF THE INVENTION

Problems to be Solved by the Invention

However, with the configuration described in Patent document 1, electromagnetic valves are disposed at positions respectively at the upstream and downstream of the fragrance retention container for opening/closing of the fragrance retention container, it becomes expensive when plural fragrant ingredients are to be supplied. Further, since there is no description on a specific shape of the fragrance device, feasibility is uncertain. Further, with the configuration described in Patent document 2, there is a fear of leakage occurrence of a fragrant ingredient while sealing ability of the cartridge cannot be maintained during non-supplying of the fragrant ingredient due to abrasion of a seat of the support plate caused by rotation of the adjusting parts when intermittent opening/closing control is performed. In addition, there is a fear of noise occurrence due to sliding of the adjusting parts.

Further, with the configuration described in Patent document 1, although the supplying amount of the fragrant ingredient can be adjusted by varying supplying time of the fragrant ingredient, odor intensity of the fragrant ingredient cannot be adjusted. With the configuration described in Patent document 3, although odor intensity of the fragrant ingredient can be adjusted, the structure to be actualized is complicated.

Further, with the configuration described in Patent document 2, since opening/closing of the fragrance retention container is controlled by sandwiching and sliding a packing between an annular seat and adjusting parts, there are problems such as short service lifetime due to packing abrasion, noise at the time of packing sliding, and unintentional volatilization of the fragrant ingredient due to packing abrasion. In order to solve such problems, it is possible to consider a fragrance device for a vehicle which intermittently supplies a fragrant ingredient with a structure that opening/closing of an opening portion of the fragrance retention container is performed by a door. With the above configuration, the fragrance device can be downsized and durability of the fragrance device can be improved as solving problems of packing abrasion and sliding noise which has been problems of Patent document 2. However, the structure to open/close the opening portion with the door causes increase of sealing positions at an opening portion of a main body internal space and the opening portion of the fragrance retention container and increase in part count.

The present invention provides a high-durability fragrance device for a vehicle capable of supplying plural fragrant ingredients without noise occurrence at the time for supplying and non-supplying of the fragrant ingredients with a simple drive mechanism.

Means for Solving the Problems

In order to address the above issues, the fragrance device for a vehicle according to the present invention adopts a structure to control supplying of air flow which contains a fragrant ingredient with a single actuator and a single cam.

Specifically, according to the invention of the present application, the fragrance device for a vehicle capable of supplying a fragrant ingredient of a fragrant agent to the inside of the vehicle as being contained in air flow, includes: at least a fragrance retention container including an accommodation space to accommodate the fragrant agent, an air inlet opening portion and an air outlet opening portion; a main body to which the fragrance retention container is attached and which includes an inlet passage to inpour air to the air inlet opening portion, an outlet passage to outpour air containing the fragrant ingredient from the air outlet opening portion, an inlet passage opening/closing door to open/close the air inlet opening portion, and an outlet passage opening/closing door to open/close the air outlet opening portion; an actuator fixed to the main body; a cam which is connected to the actuator and which rotationally drives a rotary shaft of the inlet passage opening/closing door and a rotary shaft of the outlet passage opening/closing door.

In the fragrance device for a vehicle according to the present invention, it is preferable that the inlet passage opening/closing door and the outlet passage opening/closing door are attached to a single rotary shaft at positions where opening/closing of the air inlet opening portion and the air outlet opening portion are synchronized. According to the above structure, since the number of the rotary shafts to which the inlet passage opening/closing door and the outlet passage opening/closing door are arranged can be reduced, the fragrance device for a vehicle having the simpler structure can be obtained. In addition, the fragrant ingredient can be prevented from being wasted when supplying of the fragrant ingredient is kept stopped.

According to another aspect of the present invention, in the fragrance device for a vehicle, it is preferable that the fragrance retention container includes plural accommodation spaces for respectively accommodating plural fragrant agents, and the air inlet opening portion and the air outlet opening portion for each accommodation space; the main body includes the inlet passage opening/closing door for each air inlet opening portion and the outlet passage opening/closing door for each air outlet opening portion; and the inlet passage and the outlet passage become a directly-connected passage when all of the air inlet opening portions and the air outlet opening portions are closed. With the above structure, since the fragrant ingredient remaining in the outlet passage can be ejected when the fragrant ingredient is not supplied, the fragrance device for a vehicle can supply only a different fragrant ingredient when the different fragrant ingredient is to be supplied.

According to another aspect of the present invention, in the fragrance device for a vehicle, it is preferable that the fragrance retention container includes plural accommodation spaces for respectively accommodating plural fragrant agents, and the air inlet opening portion and the air outlet opening portion for each accommodation space; the main body includes the inlet passage opening/closing door for each air inlet opening portion and the outlet passage opening/closing door for each air outlet opening portion; and the cam causes a mode in which all of the inlet passage opening/closing doors and the outlet passage opening/closing doors are closed to occur on the way when the inlet passage opening/closing door and the outlet passage opening/closing door corresponding to the air inlet opening portion and the air outlet opening portion of an accommodation space are being switched from an opened state to a closed state and the inlet passage opening/closing door and the outlet passage opening/closing door corresponding to the air inlet opening portion and the air outlet opening portion of another accommodation space are being switched from a closed state to an opened state. With the above structure, the fragrance device for a vehicle can supply plural fragrant ingredients without being mixed when switching the plural fragrant ingredients.

According to another aspect of the present invention, in the fragrance device for a vehicle, it is preferable that the cam causes a mode in which all of the inlet passage opening/closing doors and the outlet passage opening/closing doors are closed to occur on the way when the inlet passage opening/closing door and the outlet passage opening/closing door corresponding to the air inlet opening portion and the air outlet opening portion of an accommodation space are being switched from an opened state to a closed state and the inlet passage opening/closing door and the outlet passage opening/closing door corresponding to the air inlet opening portion and the air outlet opening portion of another accommodation space are being switched from a closed state to an opened state. With the above structure, the fragrance device for a vehicle can supply plural fragrant ingredients without being mixed when switching the plural fragrant ingredients. Then, since the fragrant ingredient remaining in the outlet passage can be ejected in the act of switching the fragrant ingredients, it is possible to supply only a different fragrant ingredient when the different fragrant ingredient is to be supplied.

According to another aspect of the present invention, in the fragrance device for a vehicle, it is preferable that the fragrance retention container includes respective pluralities of the fragrant agents, the air inlet opening portions, the air outlet opening portions, the inlet passage opening/closing doors, and the outlet passage opening/closing doors; the inlet passage opening/closing doors and the outlet passage opening/closing doors are attached respectively to a separate rotary shaft at positions where opening/closing of the air inlet opening portions and the air outlet opening portions are synchronized; the main body includes a shortcut hole which connects the inlet passage and the outlet passage; and any one of the inlet passage opening/closing doors closes an inlet of the shortcut hole when opens the air inlet opening portion and any one of the outlet passage opening/closing doors closes an outlet of the shortcut hole when opens the air outlet opening portion. With the above structure, the fragrance device for a vehicle can supply the fragrant ingredient by effectively utilizing air flow when supplying the fragrant ingredient.

In the fragrance device for a vehicle according to the present invention, it is preferable that the fragrance retention container includes a plurality of the accommodation spaces for accommodating fragrant agents; and volumes of the accommodation spaces respectively differ for each fragrant agent. Since the control means to supply the fragrant ingredient to the inside of the vehicle adopts a simple structure and sets an accumulation amount of the fragrant ingredient to be supplied for each fragrant ingredient, it is possible to provide the device capable of supplying the respective fragrant ingredients at appropriate odor intensity.

Further, in the fragrance device for a vehicle according to the present invention, it is preferable that the inlet passage opening/closing door and the outlet passage opening/closing door open and close the air inlet opening portion and the air outlet opening portion in synchronization with each other; the air inlet opening portion and the air outlet opening portion disposed at one accommodation space are being opened or closed when the air inlet opening portion and the air outlet opening portion disposed at the other accommodation space are closed; and the air inlet opening portion and the air outlet opening portion disposed at the other accommodation space are being opened or closed when the air inlet opening portion and the air outlet opening portion disposed at the one accommodation space are closed. With the above structure, since the fragrant ingredient can be accumulated in the accommodation space, the fragrant ingredient can be supplied at appropriate odor intensity with simple control.

In the fragrance device for a vehicle according to the present invention, it is preferable that the fragrant agent is solid-like or is a ceramic body supporting a fragrant agent. With the above structure, it is possible to provide the low-cost fragrance device which can be easily handled during manufacturing without necessity of leakage-prevention measures for manufacturing the fragrance retention container.

In the fragrance device for a vehicle according to the present invention, it is preferable that the fragrant agents are a fragrant agent A being large and heavy and a fragrant agent B being smaller and lighter than the fragrant agent A; the fragrant agent A is sized to be incapable of being accommodated in a small-volume accommodation space X and sized to be capable of being accommodated in a large-volume accommodation space Y; and the fragrant agent B is sized to be capable of being accommodated in the accommodation space X. With the above structure, it is possible to easily discriminate between kinds by differently setting weight of the fragrant agent A and the fragrant agent B, and then, it is possible to detect erroneous accommodation by measuring weight even if the fragrant agent B is accommodated in the accommodation spaces X and Y by mistake. Further, it is easy to recognize combination between the kinds of the fragrant agents and the accommodation spaces to be accommodated by differently setting dimensions. When the fragrant agent A is sized not to be capable of being accommodated in the small-volume accommodation space X, it is possible to prevent erroneous accommodation of the fragrant agent A into the accommodation space X. Accordingly, productivity and operability can be improved at the time of manufacturing the fragrance device or at the time of replacing the fragrant agent.

In the fragrance device for a vehicle according to the present invention, it is preferable that the fragrant agents are an fragrant agent having a large detection threshold value of a fragrant ingredient and a fragrant agent having a smaller detection threshold value than that of the fragrant agent; and the fragrant agent having the large detection threshold value is accommodated in a large accommodation space and the fragrant agent having the small detection threshold value is accommodated in a smaller accommodation space than the large accommodation space. With the above structure, since the fragrant ingredient of the fragrant agent having the small detection threshold value can be supplied relatively less and the fragrant ingredient of the fragrant agent having the large detection threshold value can be supplied relatively more, it is possible to supply the fragrant ingredients as being adjusted at constant odor intensity regardless of the detection threshold values.

In the fragrance device for a vehicle according to the present invention, it is preferable that the fragrant agents are a fragrant agent having a large evaporation rate of a fragrant ingredient and a fragrant agent having a smaller evaporation rate than the fragrant agent; (I) the fragrant agent having the large evaporation rate is accommodated in a small accommodation space and the fragrant agent having the small evaporation rate is accommodated in a larger accommodation space than the small accommodation space, or (II) the fragrant agent having the large evaporation rate is accommodated in a large accommodation space and the fragrant agent having the small evaporation rate is accommodated in a smaller accommodation space than the large accommodation space. With the structure of (I), the fragrant ingredient of the fragrant agent having the large evaporation rate can be prevented from being volatilized beyond necessity and the fragrant ingredient of the fragrant agent having the small evaporation rate can ensure to provide a sufficient accumulation amount. Accordingly, the fragrant ingredients can be supplied as being adjusted at constant odor intensity regardless of the evaporation rates. Further, with the structure of (II), it is possible to reduce difference of the time until the fragrant ingredient reaches the saturated vapor pressure as being pervaded in the accommodation space (i.e., the time until accumulation is completed) between the fragrant ingredient of the fragrant agent having the small evaporation rate and the fragrant ingredient of the fragrant agent having the large evaporation rate even when the accommodation volumes are set to be different.

In the fragrance device for a vehicle according to the present invention, it is preferable that the accommodation spaces are set to have different volumes owing to a partitioning ratio of the accommodation spaces with an intra-container partition plate or owing to a volume of a dummy member accommodated in the accommodation space. With the structure of the former, the plural accommodation spaces can be formed easily and inexpensively. With the structure of the latter, the volume of the accommodation space can be easily varied corresponding to the kind of the fragrant agent for changing the fragrant agent.

In the fragrance device for a vehicle according to the present invention, it is preferable that the fragrance retention container is formed of resin or resin-based material. With the above structure, the fragrance device for a vehicle can be lightened.

In the fragrance device for a vehicle according to the present invention, it is preferable that the resin is polypropylene; and the fragrance retention container is formed to have thickness of being not less than 1.8 mm and not more than 3.2 mm With the above structure, since polypropylene-based resin which is widely used for cases of vehicle-use air-conditioning devices can be used for the material of the fragrance retention container, the material can be easily procured. In addition, separating for recycling is not required for the fragrance retention container as using the same material as that of the vehicle-use air-conditioning device. It is possible to delay speed of permeation of fragrant ingredients to resin by setting the thickness of the fragrance retention container to 1.8 mm or more. Accordingly, unintentional volatilization of fragrant ingredients can be prevented during a period of service lifetime of the fragrance device. Then, deformation due to sink occurring at the time of resin molding can be prevented by setting the thickness to 3.2 mm or less.

According to the fragrance device for a vehicle of the present invention, in a sealing component made of elastic material to be used for the fragrance device for a vehicle according to the present invention, the vehicle-use fragrance device adds a fragrant ingredient of the fragrant agent to air flow of an air-conditioning device as including a fragrance retention container which includes an accommodation space to accommodate a fragrant agent and a container opening portion, and a main body including a main body internal space to be an air flow passage, a main body opening portion, and a passage opening/closing door to open/close the main body opening portion from the inside, and as the fragrance retention container being attached to the main body in a state that the accommodation space and the main body internal space are communicated via the container opening portion and the main body opening portion; the sealing component is sandwiched between mating faces of the fragrance retention container and the main body and is provided with a hole portion which causes communication between the accommodation space and the main body internal space, a door side pressure-contact portion in which an opening portion at one end side of the hole portion is closed as being pressure-contacted with a door face when the passage opening/closing door is closed while the opening portion at the one end side is placed in the main body internal space, and a container side pressure-contact portion which seals the container opening portion as being sandwiched and pressure-contacted by the fragrance retention container and the main body while the opening portion of the other end side of the hole portion is placed between the fragrance retention container and the main body or in the accommodation space; and the door side pressure-contact portion and the container side pressure-contact portion are integrally formed. It is possible to provide the durable sealing component having less sealing positions and less part count so that the desired fragrant ingredient can be supplied when desired and unintentional volatilization of fragrant ingredients can be prevented when not desired.

In the sealing component for a vehicle-use fragrance device according to the present invention, it is preferable that the container side pressure-contact portion seals the main body opening portion. With the above structure, the sealing component can reliably prevent leakage from the main body internal space without relation to opening/closing of the passage opening/closing door.

In the sealing component for a vehicle-use fragrance device according to the present invention, it is preferable that a center portion of a section of the door side pressure-contact portion placed in the main body internal space has a larger outer diameter than the diameter of the main body opening portion. With the above structure, the sealing component can be assembled easily and reliably when being assembled to the main body opening portion. Further, when the opening portion at one end side of the hole portion is pressure-contacted by the passage opening/closing door, the opening portion follows without straining. Accordingly, sealing ability between the passage opening/closing door and the sealing component can be improved.

The sealing component for a vehicle-use fragrance device according to the present invention preferably includes plural through pathways respectively constituted with the hole portion, the door side pressure-contact portion and the container side pressure-contact portion, wherein the whole is integrally formed. With the above structure, the sealing component can be formed as one part count even when the sealing components includes plural through pathways. Accordingly, operability can be improved for assembling or replacing the sealing component.

The sealing component for a vehicle-use fragrance device according to the present invention is preferably formed of elastomer. With the above structure, the sealing component can obtain superior elasticity, durability and barrier properties against fragrant ingredients owing to natural characteristics of elastomer.

The sealing component for a vehicle-use fragrance device according to present invention is preferably integrally formed with the fragrance retention container. With the above structure, owing to integration of the fragrance retention container and the sealing component, reliable sealing can be obtained while reducing part count. Further, since the sealing component can be assembled or replaced along with the fragrance retention container, it is possible to eliminate a risk of missing of the sealing component. Then, when the fragrance retention container is assembled to the main body, sealing ability due to the sealing component is inevitably ensured. Accordingly, operability of assembling and robustness can be improved. Further, since elastomer can be thermally deposited, productivity can be improved in the process to integrate the sealing component with the fragrance retention container.

The sealing component for a vehicle-use fragrance device according to the present invention is preferably formed of butyl rubber. With the above structure, the sealing component can obtain superior barrier properties against the fragrant ingredient owing to low permeability to gases of butyl rubber.

The sealing component for a vehicle-use fragrance device according to the present invention is preferably formed of silicone series rubber. With the above structure, the sealing component can obtain superior durability owing to high thermostability of silicone series rubber.

Here, the above structures can be combined to the extent possible.

Effects of the Invention

The present invention provides a high-durability fragrance device for a vehicle capable of supplying plural fragrant ingredients without noise occurrence at the time for supplying and non-supplying of the fragrant ingredients with a simple drive mechanism.

BRIEF DESCRIPTION OF THE DRAWINGS

FIG. 4 is schematic view illustrating the relation between an open/close state of an inlet passage opening/closing door and an outlet passage opening/closing door and a rotation state of a cam viewing from the opposite side to direction S in FIG. 1.

FIG. 6 is a schematic view illustrating operation of the fragrance device 100 for a vehicle according to the first embodiment of the present invention and the flow of air flow as the front view being a perspective view viewing FIG. 1 from direction S.

FIG. 7 is a schematic sectional view of a fragrance device 101 for a vehicle according to a second embodiment.

FIG. 8 is a schematic view illustrating operation of the fragrance device 101 for a vehicle according to the second embodiment and flow of air flow.

FIG. 9 is a schematic sectional view of a fragrance device 102 for a vehicle according to a third embodiment.

FIG. 10 is a schematic view illustrating operation of the fragrance device 102 for a vehicle according to the third embodiment and flow of air flow.

FIG. 11 is a schematic view illustrating plural accommodation spaces respectively having a different volume in the fragrance retention container. FIG. 11A illustrates a structure of being divided by an intra-container partition plate. FIG. 11B illustrates another structure of being divided by an intra-container partition plate. FIG. 11C illustrates a structure that a different volume is obtained by accommodating a dummy member in one accommodation space of accommodation spaces having the same volume.

FIG. 12 is a schematic sectional view illustrating operation of accumulating and supplying of the fragrance device 100 for a vehicle according to the present invention.

FIG. 13 is a schematic sectional view illustrating operation accumulating and supplying of the fragrance device 101 for a vehicle according to the second embodiment.

FIG. 17 is a schematic sectional view of the main body in FIG. 14 and the sealing component according to the first embodiment to be incorporated therein. FIG. 17A illustrates a state that one door is opened and the other door is closed. FIG. 17B illustrates a state that all doors are closed. FIG. 17C illustrates a state that the one door is closed and the other door is opened.

FIG. 19 is a schematic sectional view of the main body in FIG. 14 and the sealing component according to the second embodiment which is thermally deposited to the fragrance retention container.

BEST MODE(S) FOR CARRYING OUT THE INVENTION

Figure 1:
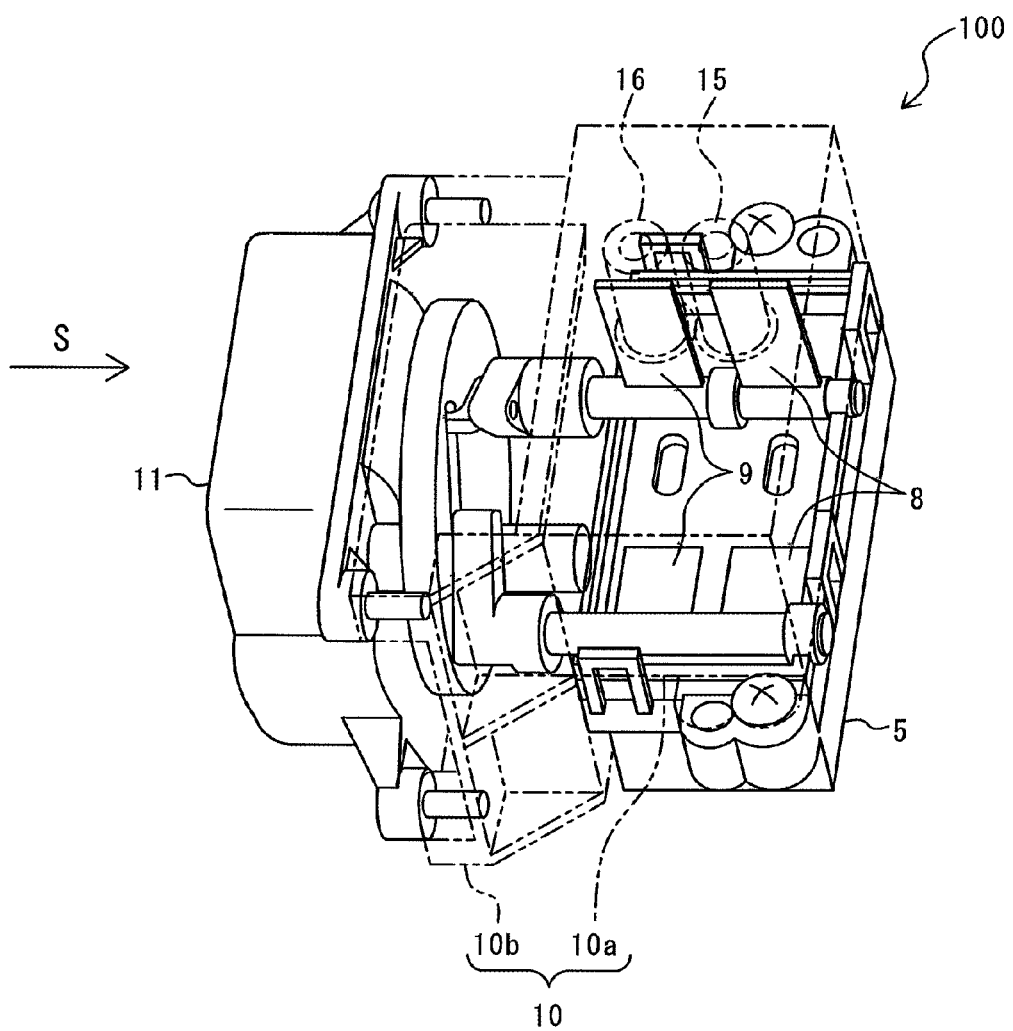
FIG. 1 is a perspective view of a fragrance device 100 for a vehicle according to a first embodiment.

In the following, an aspect of the present invention will be described with reference to the attached drawings. Embodiments described in the following are examples of the present invention. The present invention is not to be limited to the following embodiments. Here, in the present specification and the drawings, structural elements having the same reference numeral denote mutually the same. Various modifications can be performed as long as the effects of the present invention are obtained.

Figure 2:
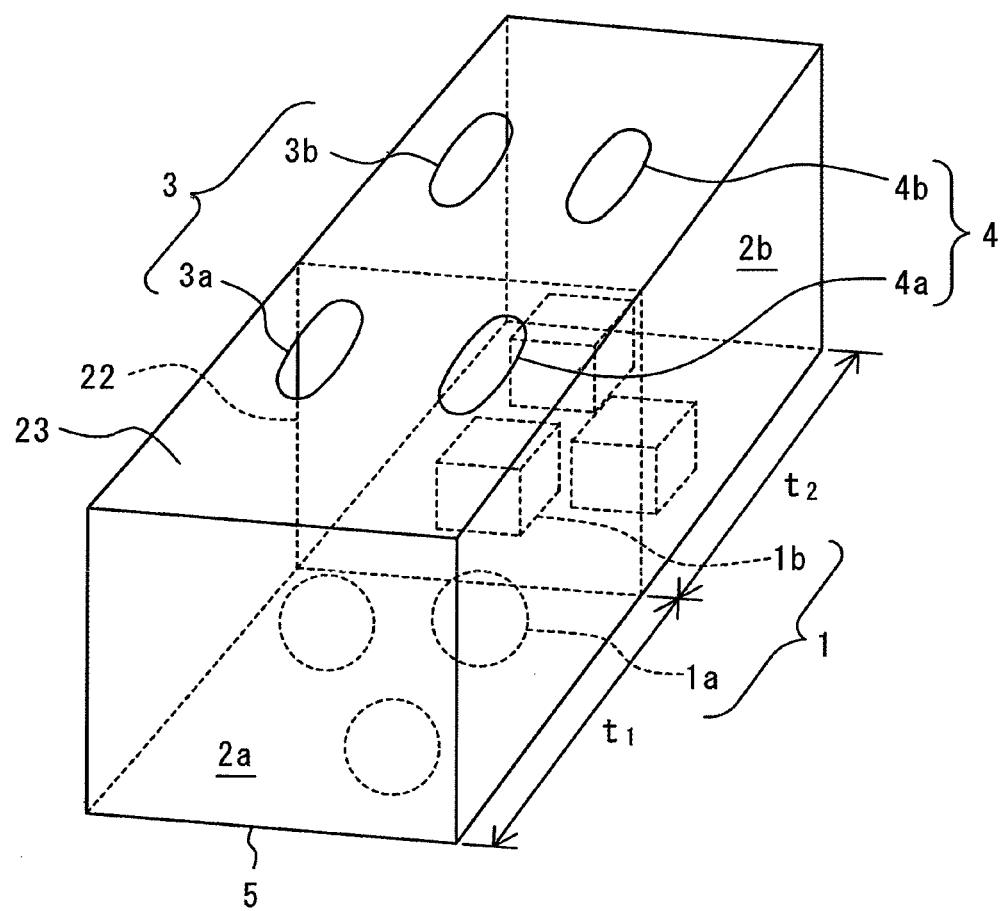
FIG. 2 is a schematic view of a fragrance retention container of the fragrance device for a vehicle.
Figure 3:
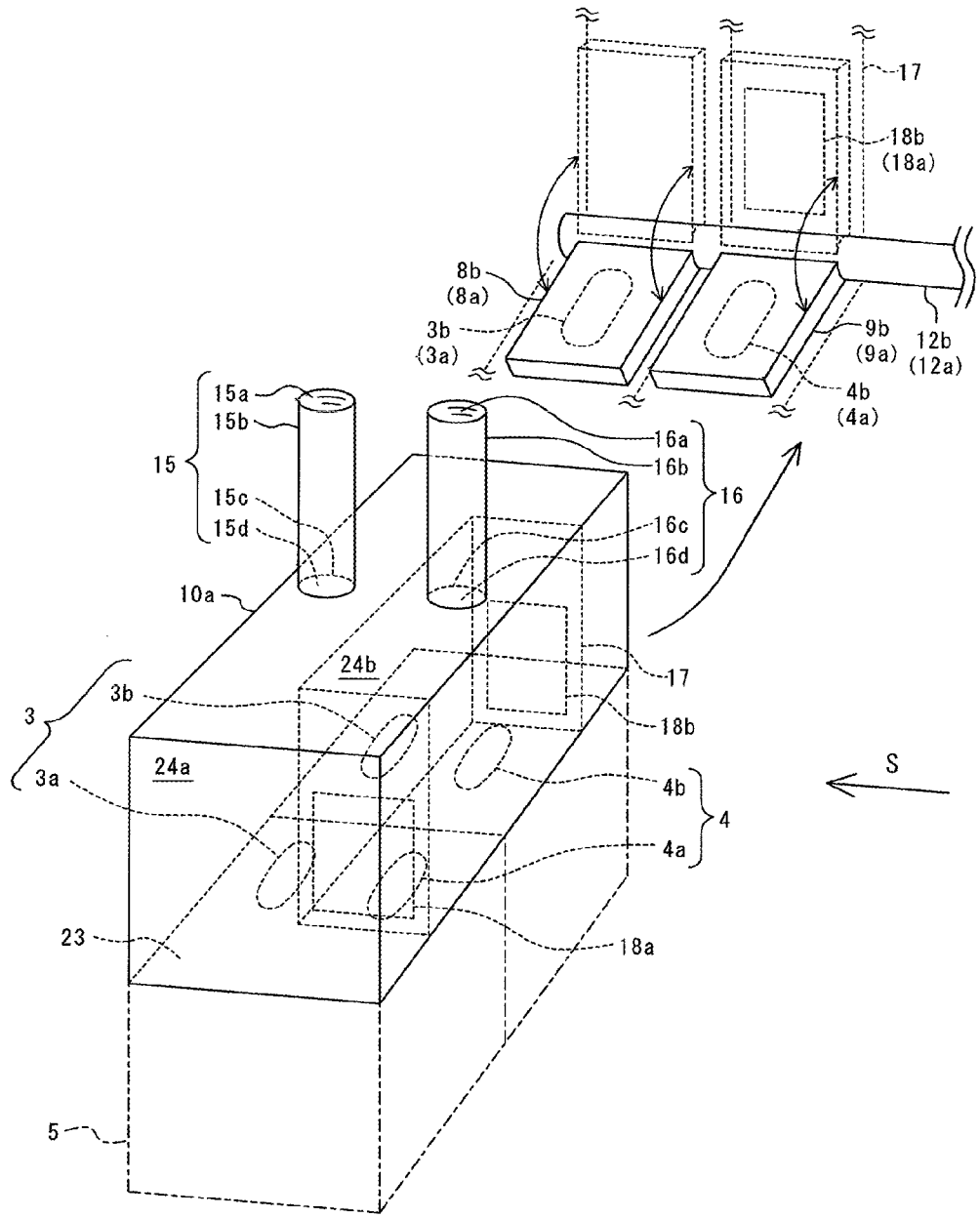
FIG. 3 is a schematic view of a main body including a door which performs opening/closing of an air inlet opening portion and an air outlet opening portion viewing from direction S in FIG. 1.
Figure 4A:
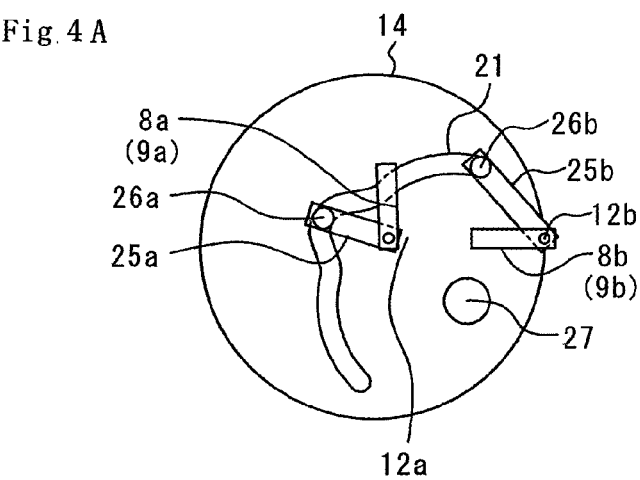
FIG. 4A illustrates a state that one door is opened and the other door is closed.
Figure 4B:
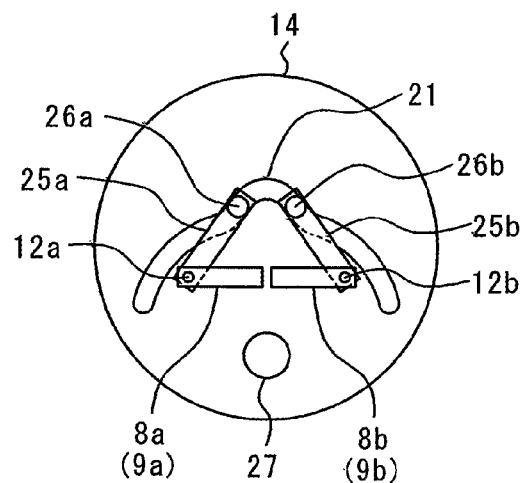
FIG. 4B illustrates a state that all doors are closed.
Figure 4C:
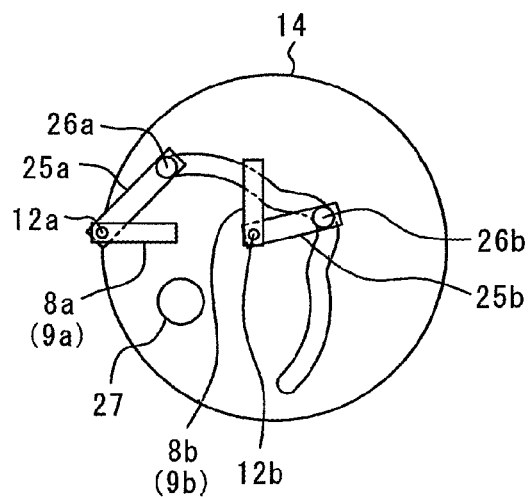
FIG. 4C illustrates a state that the one door is closed and the other door is opened.
Figure 5:
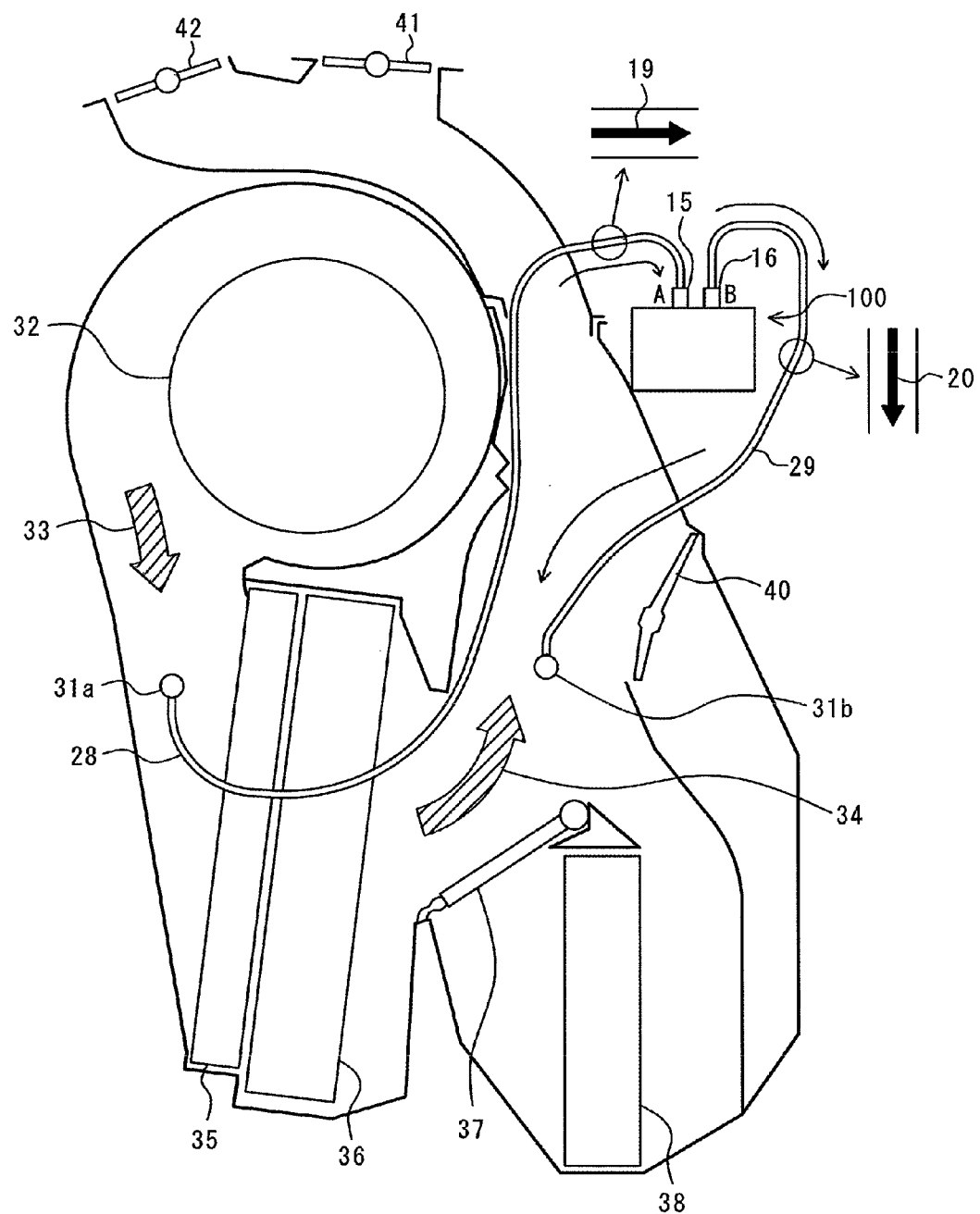
FIG. 5 is a schematic view of the connection relation with a vehicle-use air-conditioning device as illustrating arrangement of the fragrance device for a vehicle.

A fragrance device 100 for a vehicle according to the first embodiment will be described with reference to FIGS. 1 to 5. FIG. 1 is a perspective view of the fragrance device 100 for a vehicle according to the first embodiment. FIG. 2 is a schematic view of a fragrance retention container of the fragrance device for a vehicle. FIG. 3 is a schematic view of a main body including a door which performs opening/closing of an air inlet opening portion and an air outlet opening portion viewing from direction S in FIG. 1. FIG. 4 is a schematic view illustrating the relation between an open/close state of an inlet passage opening/closing door and an outlet passage opening/closing door and a rotation state of a cam viewing from the opposite side to direction S in FIG. 1. FIG. 4A illustrates a state that one door is opened and the other door is closed. FIG. 4B illustrates a state that all doors are closed. FIG. 4C illustrates a state that the one door is closed and the other door is opened. FIG. 5 is a schematic sectional view of the connection relation with a vehicle-use air-conditioning device as illustrating arrangement of the fragrance device for a vehicle.

As illustrated in FIGS. 1 to 3, the fragrance device 100 for a vehicle according to the first embodiment includes at least one fragrance retention container 5 having an accommodation space 2 to accommodate a fragrant agent 1, an air inlet opening portion 3 and an air outlet opening portion 4 to be capable of supplying a fragrant ingredient of the fragrant agent 1 to the inside of the vehicle as being contained in air flow. The fragrance device 100 is provided with a main body 10 to which the fragrance retention container 5 is attached and which includes an inlet passage 6 to inpour air to the air inlet opening portion 3, an outlet passage 7 to outpour air containing the fragrant ingredient from the air outlet opening portion 4, an inlet passage opening/closing door 8 to open/close the air inlet opening portion 3 and an outlet passage opening/closing door 9 to open/close the air outlet opening portion 4, a single actuator 11 fixed to the main body 10, and a single cam 14 connected to the actuator 11 to rotationally drive a rotary shaft 12 of the inlet passage opening/closing door 8 and a rotary shaft 12 of the outlet passage opening/closing door 9.

For example, the fragrant agent 1 is geraniol, nerol, linalool, nootkatone or menthol. At least one kind of the fragrant agent 1 is used. Here, it is also possible to adopt two or more kinds of the fragrant agents 1. When two or more kinds of the fragrant agents 1 are adopted, it is preferable to combine a relax-type fragrant agent and a refresh-type fragrant agent. For example, the relax-type fragrant agent is Forest, Lemon, Rose, Lavender, Pine or Ylangylang. For example, the refresh-type fragrant agent is Mint, Floral, Musk, Menthol, Japanese mint, Peppermint or Eucalyptus. It is also possible to use the above fragrant agents as being diluted with solvent such as dipropylene glycol, methoxymethyl butanol and liquid paraffin.

It is preferable that the fragrant agent 1 is specifically formed as a solid fragrant agent, a ceramic body to which fragrant agent is supported and the like. In the case of using a gaseous fragrant agent, for example, handling is difficult owing to leakage-prevention measures for manufacturing the fragrance retention container 5 and cost is increased owing to necessity for a pressure container. In addition, there is a risk when being mounted on a vehicle. Alternatively, in the case of using a liquid fragrant agent, handling is difficult owing to leakage-prevention measures for manufacturing the fragrance retention container 5 and cost is increased owing to maintaining liquid-tightness. The fragrant agent 1 is preferably used as being put in a bag made of film which is permeable for fragrant ingredients or mesh. It is possible to prevent noise to be generated by shaking of the fragrant agent 1 in the accommodation space 2.

When a plurality kinds of fragrant agents 1 are accommodated, it is preferable that either or both of dimensions and weight are made different between the fragrant agents firstly to easily discriminate among kinds and further to easily recognize combination between the kinds of the fragrant agents and the accommodation spaces to be accommodated. Furthermore, it is also possible to vary saturated vapor pressure as diluting a fragrant ingredient in solvent. Accordingly, it is possible to adjust the amount of the fragrant ingredient to be pervaded.

As illustrated in FIG. 1, the single fragrance retention container 5 is disposed to the fragrance device 100 for a vehicle. However, it is also possible to dispose two or more. As illustrated in FIG. 2, the fragrance retention container 5 includes an accommodation space 2a and an accommodation space 2b at the inside thereof. In the case of arranging two or more of the accommodation spaces 2, dividing is performed into the accommodation space 2a and the accommodation space 2b by partitioning the inside of the accommodation space 2 with an intra-container partition plate 22. Alternatively, it is also possible to dispose two or more of the accommodation spaces 2 by disposing a plurality of the fragrance retention containers 5. Here, width of the accommodation space 2a is denoted by $t_1$ and width of the accommodation space 2b is denoted by $t_2$. For example, the volume of the accommodation space 2a is set to be smaller than the volume of the accommodation space 2b by setting length $t_1$ to be shorter than length $t_2$. The fragrant agent 1a is accommodated in the accommodation space 2a and the fragrant agent 1b being different from the fragrant agent 1a is accommodated in the accommodation space 2b. An example to accommodate different kinds of fragrant agents is illustrated in FIG. 2. However, it is also possible to accommodate the same kinds of fragrant agents. Here, it is preferable that the fragrant agent 1a is a refresh-type fragrant agent and the fragrant agent 1b is a relax-type fragrant agent. Alternatively, it is also possible to adopt the reverse combination.

Further, the fragrance retention container 5 is formed as a detachably attachable cartridge for supplementing the fragrant agent 1. Since it is required to prevent inverted-assembling along the attaching direction to a case 10a of a main body 10, it is preferable to adopt an inverted-assembling prevention structure with a positioning pin and the like. Then, in order to facilitate manufacturing, it is preferable that the fragrance retention container 5 is made of polypropylene or polypropylene-based resin being similarly to a case of a vehicle-use air-conditioning device. In the case of using polypropylene-based resin, it is preferable that talc is contained therein. The ratio of talc is 10 to 30 wt %, for example. Since it is possible to use polypropylene-based resin which is widely used for cases of vehicle-use air-conditioning devices, material can be easily procured and manufacturing can be performed with injection molding similarly to cases of vehicle-use air-conditioning devices. Accordingly, productivity can be increased. In addition, although the fragrance device 100 for a vehicle is attached to a vehicle-use air-conditioning device, separating for recycling is not required as using the same material as that of the vehicle-use air-conditioning device. Here, since polypropylene (PP) has high permeability for fragrant ingredients, there is a fear of being resolved as being reacted with fragrant ingredients. Accordingly, it is also possible to adopt high crystal PP or PP on which metal such as aluminum is deposited. Alternatively, instead of PP, it is also possible to adopt polyethylene terephthalate resin (PET) as the resin. It is preferable that the fragrance retention container 5 is formed to have thickness of being not less than 1.8 mm and not more than 3.2 mm to prevent permeation of fragrant ingredients and sink when molding. It is possible to delay speed of leakage due to permeation of fragrant ingredients to resin by setting the thickness to 1.8 mm or more. Accordingly, unintentional volatilization of fragrant ingredients can be prevented during a period of service lifetime of the fragrance device 100 for a vehicle. Then, deformation due to sink occurring at the time of resin molding can be prevented by setting the thickness to 3.2 mm or less.

Regarding the accommodation space 2a for accommodating the fragrant agent 1a and the accommodation space 2b for accommodating the fragrant agent 1b, it is preferable to enable to supply fragrant ingredients of the fragrant agents 1a, 1b respectively for an appropriate amount by setting the volume of the accommodation space 2a and the accommodation space 2b to be different for each fragrant agent and by setting the fragrant ingredient pervaded in the accommodation space 2a or the accommodation space 2b to be a supply amount for one time.

As illustrated in FIG. 2, an air inlet opening portion 3a and an air outlet opening portion 4a are connected to the accommodation space 2a. Further, an air inlet opening portion 3b and an air outlet opening portion 4b are connected to the accommodation space 2b. The air inlet opening portion 3 and the air outlet opening portion 4 are preferably arranged at the same face of a container top face 23 of the fragrance retention container 5 and are arranged respectively to a size to be capable of being sealed by a door which performs opening/closing. The air inlet opening portion 3 may be formed in any shape as long as air flow 19 is not disrupted. The air outlet opening portion 4 may be formed in any shape as long as air flow 20 containing a fragrant ingredient is not disrupted. The air inlet opening portion 3 inpours the air flow 19 into the accommodation space 2 and the air outlet opening portion 4 outpours the air flow 20 containing the fragrant ingredient from the accommodation space 2.

As illustrated in FIG. 3, an inlet 15 having an inlet opening portion 15a at the distal end of an inlet pipe 15b and an outlet 16 having an outlet opening portion 16a at the distal end of an outlet pipe 16b are arranged at a top face of the case 10a of the main body 10. The case 10a is located above the fragrance retention container 5. A bottom face of the case 10a is formed open and is closed with a top face 23 of the fragrance retention container 5.

A partition plate 17 in the case 10a is arranged in the longitudinal direction to surround the air outlet opening portion 4, so that the space in the case 10a is divided into two spaces of an inlet side space 24a and an outlet side space 24b. A partition plate opening portion 18a formed at the partition plate 17 is a hole being adjacent to the air outlet opening portion 4a. A partition plate opening portion 18b formed at the partition plate 17 is a hole being adjacent to the air outlet opening portion 4b. The partition plate opening portion 18a is sized to be capable of being sealed by an outlet passage opening/closing door 9a which performs opening/closing of the air outlet opening portion 4a. The partition plate opening portion 18b is sized to be capable of being sealed by an outlet passage opening/closing door 9b which performs opening/closing of the air outlet opening portion 4b. When the air inlet opening portion 3a and the air outlet opening portion 4a are closed, the partition plate opening portion 18a can pass air flow therethrough from the inlet side space 24a to the outlet side space 24b. When the air inlet opening portion 3b and the air outlet opening portion 4b are closed, the partition plate opening portion 18b can pass air flow therethrough from the inlet side space 24a to the outlet side space 24b.

Here, an inlet passage 6 (not illustrated) is constituted with the inlet pipe 15b, the case 10a, the partition plate 17 and the container top face 23. An outlet passage 7 (not illustrated) is constituted with the container top face 23, the partition plate 17, the case 10a and the outlet pipe 16b.

As illustrated in FIG. 3, the case 10a of the main body 10 includes the inlet passage opening/closing door 8b to open/seal the air inlet opening portion 3b, the outlet passage opening/closing door 9b to open/seal the air outlet opening portion 4b, the inlet passage opening/closing door 8a to open/seal the air inlet opening portion 3a, and the outlet passage opening/closing door 9a to open/seal the air outlet opening portion 4a. The case 10a further includes a rotary shaft 12a to open/close the inlet passage opening/closing door 8a and the outlet passage opening/closing door 9a and a rotary shaft 12b to open/close the inlet passage opening/closing door 8b and the outlet passage opening/closing door 9b. Here, as illustrated in FIG. 1, the inlet passage opening/closing door 8b and the outlet passage opening/closing door 9b are arranged symmetrically with the inlet passage opening/closing door 8a and the outlet passage opening/closing door 9a respectively in a face-to-face manner.

The outlet passage opening/closing door 9a seals the partition plate opening portion 18a while the air outlet opening portion 4a is kept opened and opens the partition plate opening portion 18a while the air outlet opening portion 4a is kept sealed. The outlet passage opening/closing door 9b seals the partition plate opening portion 18b while the air outlet opening portion 4b is kept opened and opens the partition plate opening portion 18b while the air outlet opening portion 4b is kept sealed.

The inlet passage opening/closing door 8a may be formed as any opening/closing type in any shape as long as the air inlet opening portion 3a can be opened and sealed. The inlet passage opening/closing door 8b may be formed as any opening/closing type in any shape as long as the air inlet opening portion 3b can be opened and sealed. The outlet passage opening/closing door 9a may be formed as any opening/closing type in any shape as long as the air outlet opening portion 4a can be opened and sealed and the partition plate opening portion 18a can be opened and sealed. The outlet passage opening/closing door 9b may be formed as any opening/closing type in any shape as long as the air outlet opening portion 4b can be opened and sealed and the partition plate opening portion 18b can be opened and sealed. Here, the rotary shaft 12a and the rotary shaft 12b are rotated in a state of penetrating through the partition plate 17 and the case 10a.

For improving sealing ability due to the inlet passage opening/closing door 8, it is preferable to stick lining on a peripheral border of the air inlet opening portion 3 at the top face 23 of the fragrance retention container 5. For improving sealing ability due to the outlet passage opening/closing door 9, it is preferable to stick lining on a peripheral border of the air outlet opening portion 4 at the top face 23 of the fragrance retention container 5. In addition, it is preferable to stick lining on a peripheral border of the partition plate opening portion 18 for improving sealing ability due to the outlet passage opening/closing door 9.

Further, it is preferable that the inlet passage opening/closing door 8a and the outlet passage opening/closing door 9a are attached to the single rotary shaft 12a at positions where opening/closing of the air inlet opening portion 3a and the air outlet opening portion 4a is synchronized (not illustrated in FIG. 3). As illustrated in FIG. 3, it is preferable that the inlet passage opening/closing door 8b and the outlet passage opening/closing door 9b are attached to the single rotary shaft 12b at positions where opening/closing of the air inlet opening portion 3b and the air outlet opening portion 4b is synchronized. With this structure, since the rotary shaft for the inlet passage opening/closing door 8a and the rotary shaft for the outlet passage opening/closing door 9a are not required to be separately arranged, the structure is simplified with less part count. Further, since the synchronization of opening/closing between the inlet passage opening/closing door 8*a* and the outlet passage opening/closing door 9*a* can be ensured, operational reliability can be improved as a fragrance device. Furthermore, since the input passage opening/closing door 8*a* and the outlet passage opening/closing door 9*a* are simultaneously sealed, it is possible to prevent a fragrant ingredient from being wasted during non-supplying of the fragrant ingredient. The above is similar to the inlet passage opening/closing door 8*b* and the outlet passage opening/closing door 9*b*.

The main body 10 is constituted with the case 10*a* and a cover 10*b*. The cover 10*b* covers a cam 14 and a shaft 27 of an actuator 11 to prevent involution occurrence. The case 10*a* and the cover 10*b* may be formed integrally or separately.

As illustrated in FIG. 1, the actuator 11 is fixed to the cover 10*b* of the main body 10. As illustrated in FIG. 4, the shaft 27 of the actuator 11 is connected perpendicularly to the cam 14 and rotationally drives the cam 14. Any drive type may be adopted as long as being capable of rotationally driving the cam 14. In the present embodiment, the single cam 14 is arranged to the single actuator 11. An inexpensive and durable fragrance device capable of supplying plural fragrant ingredients can be actualized with a simple structure by arranging the actuator 11 and the cam 14 for one each. Here, it is also possible to arrange the actuators 11 and the cams 14 for two or more each.

As illustrated in FIG. 4, the cam 14 is formed disk-shaped. Any shape may be adopted as long as a trajectory groove 21 can be formed. In order to prevent run-out occurrence, it is preferable that the cam 14 is configured to be connected to the shaft 27 of the actuator 11 in a pierced manner and that the shaft 27 of the actuator 11 is supported at both ends thereof by the actuator 11 and the case 10*a*.

As illustrated in FIG. 4, the rotary shaft 12*a* for the inlet passage opening/closing door 8*a* and the outlet passage opening/closing door 9*a* is rotatably connected perpendicularly to an arm 25*a* at one end thereof. A pin 26*a* is arranged at the other end as being perpendicular in the opposite direction to the rotary shaft 12*a* in a projected manner. Further, the rotary shaft 12*b* for the inlet passage opening/closing door 8*b* and the outlet passage opening/closing door 9*b* is rotatably connected perpendicularly to an arm 25*b* at one end thereof. A pin 26*b* is arranged at the other end as being perpendicular in the opposite direction to the rotary shaft 12*b* in a projected manner.

The pin 26*a* and the pin 26*b* are perpendicularly inserted to the trajectory groove 21. The trajectory groove 21 may be formed with any depth as long as the pin 26*a* and the pin 26*b* can move along the trajectory groove 21. The arm 25*a* cooperatively moves the pin 26*a* along the trajectory groove 21. The rotary shaft 12*a* is rotated in accordance with the above motion, so that the inlet passage opening/closing door 8*a* and the outlet passage opening/closing door 9*a* are opened and closed. The arm 25*b* cooperatively moves the pin 26*b* along the trajectory groove 21. The rotary shaft 12*b* is rotated in accordance with the above motion, so that the inlet passage opening/closing door 8*b* and the outlet passage opening/closing door 9*b* are opened and closed. The arm 25*a* may be formed in any shape as long as the pin 26*a* and the rotary shaft 12*a* can be connected. The arm 25*b* may be formed in any shape as long as the pin 26*b* and the rotary shaft 12*b* can be connected.

As illustrated in FIG. 4, the actuator 11 rotates the cam 14 to the position illustrated in FIG. 4A by rotating the shaft 27 of the actuator 11 to the rotational left end, so that the inlet passage opening/closing door 8*a* is opened and the outlet passage opening/closing door 9*a* is opened. At the same time, the inlet passage opening/closing door 8*b* is closed and the outlet passage opening/closing door 9*b* is closed.

Next, the actuator 11 rotates the cam 14 to the position illustrated in FIG. 4B by rotating the shaft 27 of the actuator 11 to the right side against FIG. 4A, so that the inlet passage opening/closing door 8 is closed and the outlet passage opening/closing door 9 is closed.

Next, the actuator 11 rotates the cam 14 to the position illustrated in FIG. 4C by rotating the shaft 27 of the actuator 11 to the right side (i.e., the rotational right end) against FIG. 4B, so that the inlet passage opening/closing door 8*b* is opened and the outlet passage opening/closing door 9*b* is opened. At the same time, the inlet passage opening/closing door 8*a* is closed and the outlet passage opening/closing door 9*a* is closed. Subsequently, with repeated to-and-fro operation in the order of A→B→C→B→A . . . , opening/closing operation of the inlet passage opening/closing door 8 and the outlet passage opening/closing door 9 can be repeatedly performed. Alternatively, as needed basis, opening/closing operation of the inlet passage opening/closing door 8*a* and the outlet passage opening/closing door 9*a* can be repeatedly performed with repeated operation of A and B or opening/closing operation of the inlet passage opening/closing door 8*b* and the outlet passage opening/closing door 9*b* can be repeatedly performed as well with repeated operation of B and C.

In the following, an example of arrangement of the fragrance device for a vehicle according to the present invention will be described with reference to a schematic sectional view of FIG. 5. As illustrated in FIG. 5, a blower 32 installed in a vehicle-use air-conditioning device outpours air flow 33. Pressure of the air flow 33 is increased as being compressed toward a filter 35 and an evaporator 36 installed in the vehicle-use air-conditioning device. An end part 31*a* of an inlet pipe 28 is placed in the air flow 33 of which pressure is increased at the upstream side of the filter 35 and the evaporator 36. The air flow 19 being a part of the air flow 33 flowing into the end part 31*a* of the inlet pipe 28 passes through the inlet pipe 28, and then, is inpoured to the inlet passage 6 via the inlet 15 of the fragrance device 100 for a vehicle. In the fragrance device 100 for a vehicle, all or a part of the air flow 19 includes a fragrant ingredient to be the air flow 20 containing the fragrant ingredient. The air flow 20 containing the fragrant ingredient passes through the outlet pipe 29 via the outlet 16 from the outlet passage 7, and then, is outpoured from an end part 31*b* of an outlet pipe 29 placed in a blowing air flow 34 of which pressure is low at the downstream side of the filter 35 and the evaporator 36. With the arrangement to place the end part 31*a* of the inlet pipe 28 at the upstream side of the filter 35 and the evaporator 36 and to place the end part 31*b* of the outlet pipe 29 at the downstream side of the filter 35 and the evaporator 36, the air flow 20 containing the fragrant ingredient can be flowed by utilizing pressure difference of air sandwiching the filter 35 and the evaporator 36. Here, the end part 31*a* of the inlet pipe 28 and the end part 31*b* of the outlet pipe 29 may be placed at any positions as long as pressure difference is generated therebetween. Then, by respectively switching a foot door 40 which controls ventilation resistance of a passage connected to a foot outlet, a vent door 41 which controls ventilation resistance of a passage connected to a vent outlet, and a defrost door 42 which controls ventilation resistance of a passage connected to a defrost outlet, air flow is supplied to the vehicle inside respectively through the foot outlet, the vent outlet and the defrost outlet. Here, not illustrated in FIG. 5, there is a case that a side vent, a rear vent and a rear foot are arranged. In this case, it is also possible to supply the air flow 20 containing the fragrant ingredient to the vehicle inside through outlets of the above as well.

Figure 6A:
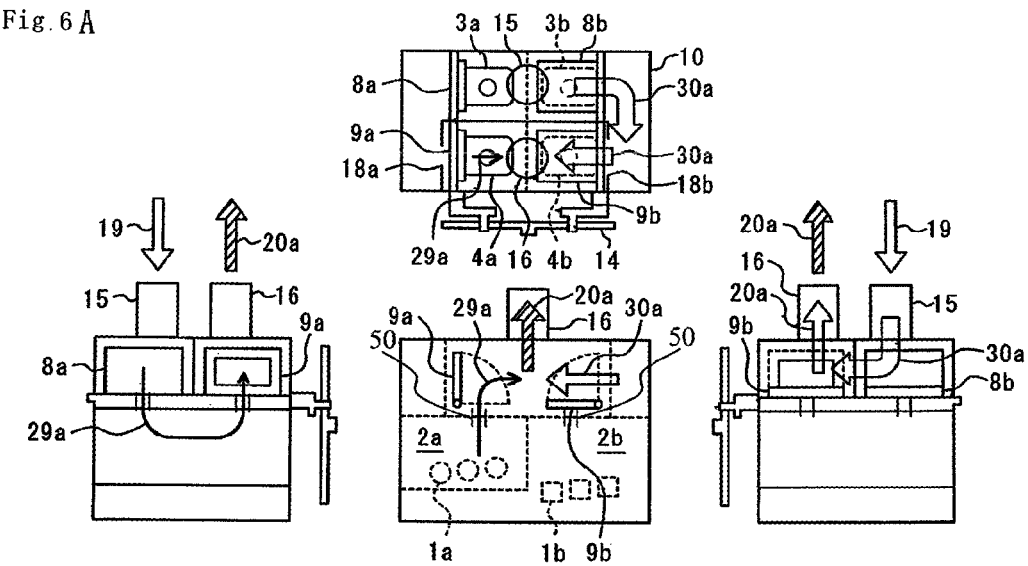
FIG. 6A illustrates a state that a fragrant ingredient of the fragrant agent 1a is supplied as one door being opened and the other door being closed.
Figure 6B:
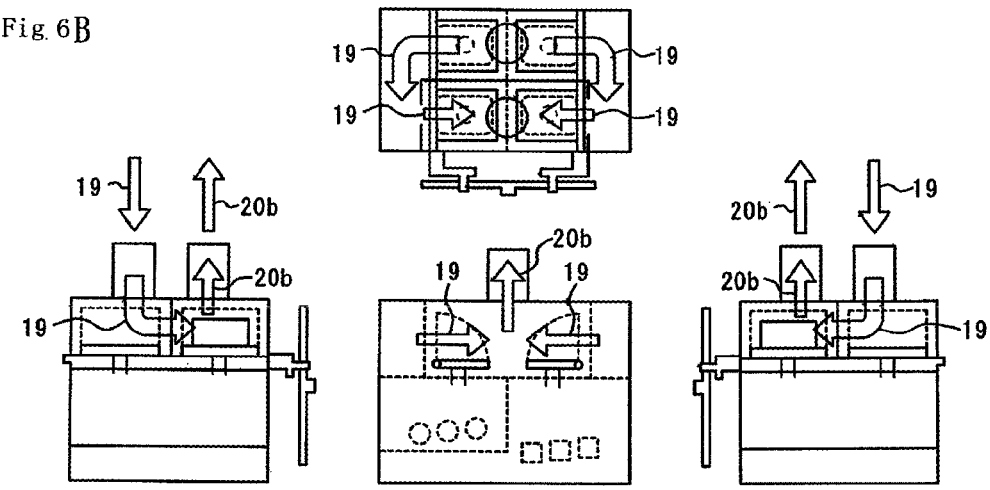
FIG. 6B illustrates a state that any fragrant ingredient is not supplied as all doors being closed.
Figure 6C:
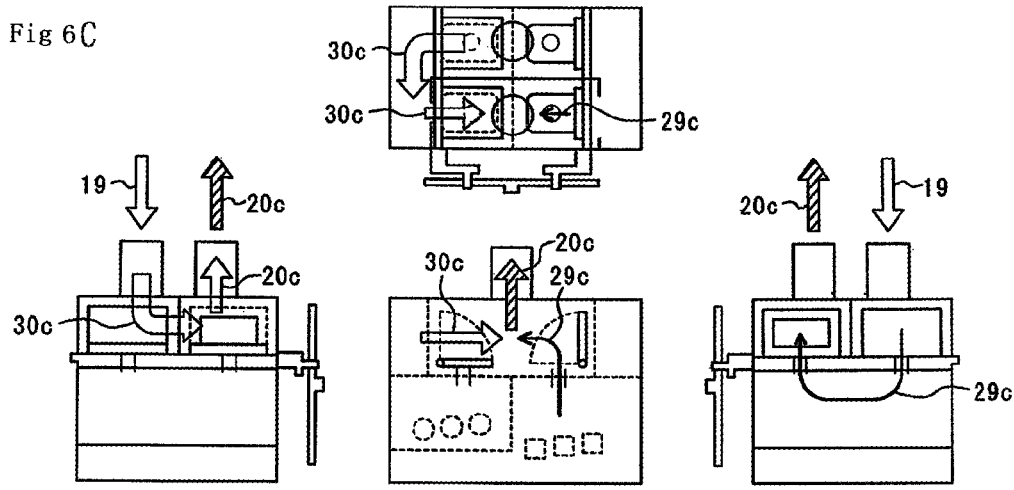
FIG. 6C illustrates a state that a fragrant ingredient of the fragrant agent 1b is supplied as the one door being closed and the other door being opened.

Next, operation of the fragrance device for a vehicle will be described with reference to FIG. 6. FIG. 6 is a schematic view illustrating operation of the fragrance device for a vehicle according to the present invention and the flow of air flow as the front view being a perspective view viewing FIG. 1 from direction S. FIG. 6A illustrates a state that the fragrant ingredient of the fragrant agent 1a is supplied as one door being opened and the other door being closed. FIG. 6B illustrates a state that any fragrant ingredient is not supplied as all doors being closed. FIG. 6C illustrates a state that the fragrant ingredient of the fragrant agent 1b is supplied as the one door being closed and the other door being opened.

As illustrated in FIG. 6A, the inlet passage opening/closing door 8a opens the air inlet opening portion 3a. The outlet passage opening/closing door 9a opens the air outlet opening portion 4a and closes the partition plate opening portion 18a. The inlet passage opening/closing door 8b closes the air inlet opening portion 3b. The outlet passage opening/closing door 9b closes the air outlet opening portion 4b and opens the partition plate opening portion 18b. A part of the air flow 19 inpoured to the inlet passage 6 from the inlet 15 flows into the accommodation space 2a from the air inlet opening portion 3a to be air flow 29a containing a fragrant ingredient as containing the fragrant ingredient of the fragrant agent 1a. The air flow 29a containing the fragrant ingredient flows to the outlet passage 7 as passing through the air outlet opening portion 4a from the inside of the accommodation space 2a. Meanwhile, other air flow 30a which is not inpoured into the accommodation space 2b from the air inlet opening portion 3b flows to the outlet passage 7 through the partition plate opening portion 18a from the inlet passage 6. Air flow 20a being mixture of the air flow 30a with the air flow 29a containing the fragrant ingredient is supplied to the vehicle inside as being outpoured from the end part 31b of the outlet pipe 29 via the outlet 16, as illustrated in FIG. 5. Then, after predetermined time passes, the state shifts to that illustrated in FIG. 6B.

As illustrated in FIG. 6B, the outlet passage opening/closing door 9a opens the partition plate opening portion 18a and the outlet passage opening/closing door 9b opens the partition plate opening portion 18b. The air flow 19 inpoured to the inlet passage 6 from the inlet 15 is outpoured from the end part 31b of the outlet pipe 29, as illustrated in FIG. 5, via the outlet passage 7 and the outlet 16 after passing through the partition plate opening portion 18a and the partition plate opening portion 18b. Accordingly, only air flow 20b which does not contain any fragrant ingredient is supplied to the vehicle inside.

Here, the main body 10 includes the inlet passage opening/closing door 8 for each air inlet opening portion 3 and the outlet passage opening/closing door 9 for each air outlet opening portion 4 and is configured so that the inlet passage 6 and the outlet passage 7 become a directly connected passage when all of the air inlet opening portion 3 and the air outlet opening portion 4 are closed. By forming the inlet passage 6 and the outlet passage 7 to be the directly-connected passage when all of the air inlet opening portion 3 and the air outlet opening portion 4 are closed, the fragrant ingredient supplied when any of the air inlet opening portion 3 and the air outlet opening portion 4 is opened can be ejected owing to the air flow 20b which does not contain any fragrant ingredient. In this manner, supplying of the fragrant ingredient is stopped by sealing the air inlet opening portion 3 and the air outlet opening portion 4, so that the fragrant ingredient can be prevented from being wasted.

The cam 14 causes a mode in which all of the inlet passage opening/closing door 8 and the outlet passage opening/closing door 9 are closed to occur on the way when the inlet passage opening/closing door 8 and the outlet passage opening/closing door 9 corresponding to the air inlet opening portion 3 and the air outlet opening portion 4 of one accommodation space 2 are being switched from an opened state to a closed state and the inlet passage opening/closing door 8 and the outlet passage opening/closing door 9 corresponding to the air inlet opening portion 3 and the air outlet opening portion 4 of the other accommodation space 2 are being switched from a closed state to an opened state. By switching plural fragrant ingredients through the mode in which all of the inlet passage opening/closing door 8 and the outlet passage opening/closing door 9 are closed, the air flow 20b which does not contain any fragrant ingredient ejects the fragrant ingredient remaining in the outlet passage 7 and the outlet pipe 29. Accordingly, the plural fragrant ingredients are not mixed.

Subsequently, the state of FIG. 6B is shifted to the state illustrated in FIG. 6C after predetermined time passes. As illustrated in FIG. 6C, the inlet passage opening/closing door 8b opens the air inlet opening portion 3b. The outlet passage opening/closing door 9b opens the air outlet opening portion 4b and closes the partition plate opening portion 18b. The inlet passage opening/closing door 8a closes the air inlet opening portion 3a. The outlet passage opening/closing door 9a closes the air outlet opening portion 4a and opens the partition plate opening portion 18a. A part of the air flow 19 inpoured to the inlet passage 6 from the inlet 15 flows into the accommodation space 2b from the air inlet opening portion 3b to be air flow 29c containing a fragrant ingredient as containing the fragrant ingredient of the fragrant agent 1b. The air flow 29c containing the fragrant ingredient flows to the outlet passage 7 passing through the air outlet opening portion 4b from the inside of the accommodation space 2b. Meanwhile, other air flow 30c which is not inpoured into the accommodation space 2b from the air inlet opening portion 3b flows to the outlet passage 7 through the partition plate opening portion 18a from the inlet passage 6. Air flow 20c being mixture of the air flow 30c with the air flow 29c containing the fragrant ingredient is supplied to the vehicle inside as being outpoured from the end part 31b of the outlet pipe 29 via the outlet 16, as illustrated in FIG. 5. Then, after predetermined time passes, the state shifts to that illustrated in FIG. 6B.

Subsequently, with repeated to-and-fro operation in the order of A→B→C→B→A . . . , supplying to the vehicle inside is repeatedly performed in the order of the air flow 20a, the air flow 20b, the air flow 20c, the air flow 20b, the air flow 20a . . . . Alternatively, as needed basis, the air flow 20a and the air flow 20b are alternately supplied to the vehicle inside with repeated operation of A and B or the air flow 20b and the air flow 20c are alternately supplied to the vehicle inside with repeated operation of B and C. Here, the air flow 20 containing a fragrant ingredient illustrated in FIG. 5 includes the air flow 20a, the air flow 20b and the air flow 20c.

Here, when the blower 32 of the vehicle-use air-conditioning device is stopped or the ignition of the vehicle is turned off in a state that a fragrant ingredient is supplied as the air inlet opening portion 3 and the air outlet opening portion 4 are opened, it is preferable that a control unit (not illustrated) performs control to close the air inlet opening portion 3 and the air outlet opening portion 4. Fragrant agents can be prevented from being wasted by closing the air inlet opening portion 3 and the air outlet opening portion 4 when a fragrant ingredient is not required to be supplied.

Further, it is also possible to arrange a door which closes the partition plate opening portion 18 in synchronization with closing of the air outlet opening portion 4 by the outlet passage opening/closing door 9 during non-supplying of a fragrant ingredient. Alternatively, it is also possible to arrange a door which closes an opening portion 15d formed at a connection portion 15c between the case 10a and the inlet pipe 15b and a door which closes an opening portion 16d formed at a connection portion 16c between the case 10a and the outlet pipe 16b in synchronization with closing of the air outlet opening portion 4 by the outlet passage opening/closing door 9 during non-supplying of a fragrant ingredient. With the above configuration, temperature adjustment can be performed for all air flow 33 during non-supplying of a fragrant ingredient, so that temperature adjustment due to the vehicle-use air-conditioning device becomes easy.

Figure 7A:
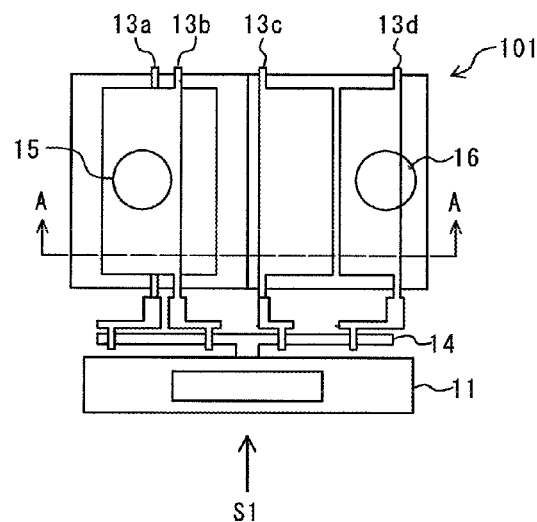
FIG. 7A is a plane view.
Figure 7C:
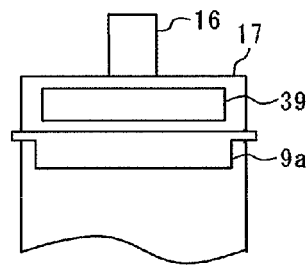
FIG. 7C is a sectional view at C-C of FIG. 7B viewing from direction S2.
Figure 7B:
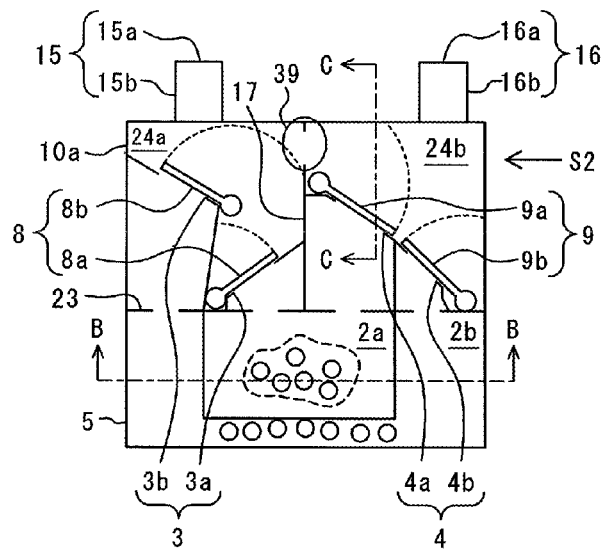
FIG. 7B is a sectional view at A-A of FIG. 7A viewing from direction S1.
Figure 7D:
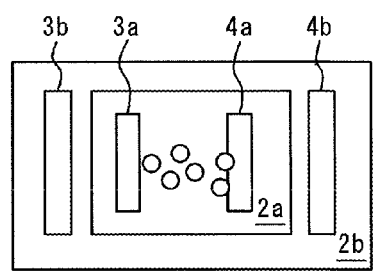
FIG. 7D is a sectional view at B-B of FIG. 7B.
Figure 8A:
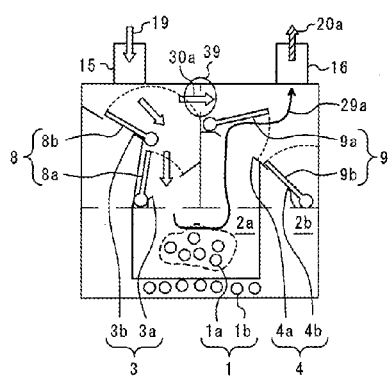
FIG. 8A illustrates a state that the fragrant ingredient of the fragrant agent 1a is supplied as one door being opened and the other door being closed.
Figure 8B:
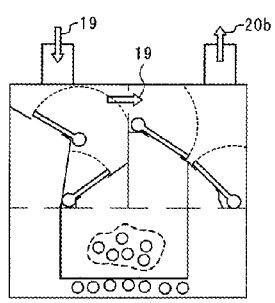
FIG. 8B illustrates a state that any fragrant ingredient is not supplied as all doors being closed.
Figure 8C:
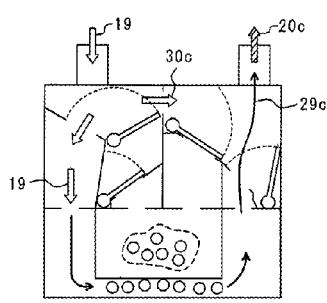
FIG. 8C illustrates a state that the fragrant ingredient of the fragrant agent 1b is supplied as the one door being closed and the other door being opened.

Next, a fragrance device 101 for a vehicle according to the second embodiment will be described with reference to FIGS. 7 and 8. FIG. 7 is a schematic sectional view of the fragrance device 101 for a vehicle according to the second embodiment. FIG. 7A is a plane view, FIG. 7B is a sectional view at A-A of FIG. 7A viewing from direction 51, FIG. 7C is a sectional view at C-C of FIG. 7B viewing from direction S2, and FIG. 7D is a sectional view at B-B of FIG. 7B. Further, FIG. 8 is an operational explanatory view of the fragrance device for a vehicle according to the second embodiment. FIG. 8A illustrates a state that the fragrant ingredient of the fragrant agent 1a is supplied as one door being opened and the other door being closed. FIG. 8B illustrates a state that any fragrant ingredient is not supplied as all doors being closed. FIG. 8C illustrates a state that the fragrant ingredient of the fragrant agent 1b is supplied as the one door being closed and the other door being opened.

The fragrance device 101 for a vehicle according to the second embodiment will be described with reference to FIG. 7. Here, since the fragrant agent 1 and the fragrance retention container 5 are similar to those of the first embodiment, description thereof is not repeated here.

As illustrated in FIG. 7, the inlet 15 having the inlet opening portion 15a at the distal end of the inlet pipe 15b and the outlet 16 having the outlet opening portion 16a at the distal end of the outlet pipe 16b are arranged at the top face of the case 10a of the main body 10. The case 10a is located above the fragrance retention container 5. The bottom face of the face 10a is formed open and is closed with the top face 23 of the fragrance retention container 5. A partition plate 17 in the case 10a is arranged to divide the space in the case 10a into two spaces of the inlet side space 24a and the outlet side space 24b. The partition plate 17 is formed with a shortcut hole 39 through which air flow can pass continuously from the inlet side space 24a to the outlet side space 24b. Here, the inlet passage 6 (not illustrated) is constituted with the inlet pipe 15b, the case 10a, the partition plate 17 and the container top face 23. The outlet passage 7 (not illustrated) is constituted with the container top face 23, the partition plate 17, the case 10a and the outlet pipe 16b.

As illustrated in FIG. 7, the case 10a of the main body 10 includes the inlet passage opening/closing door 8b to open/seal the air inlet opening portion 3b, the outlet passage opening/closing door 9b to open/seal the air outlet opening portion 4b, the inlet passage opening/closing door 8a to open/seal the air inlet opening portion 3a, and the outlet passage opening/closing door 9a to open/seal the air outlet opening portion 4a. The inlet passage opening/closing door 8a may be formed as any opening/closing type in any shape as long as the air inlet opening portion 3a can be opened and sealed. The inlet passage opening/closing door 8b may be formed as any opening/closing type in any shape as long as the air inlet opening portion 3b can be opened and sealed. The outlet passage opening/closing door 9a may be formed as any opening/closing type in any shape as long as the air outlet opening portion 4a can be opened and sealed. The outlet passage opening/closing door 9b may be formed as any opening/closing type in any shape as long as the air outlet opening portion 4b can be opened and sealed.

The case 10a further includes a rotary shaft 13a to open/close the inlet passage opening/closing door 8a, a rotary shaft 13c to open/close the outlet passage opening/closing door 9a, a rotary shaft 13b to open/close the inlet passage opening/closing door 8b, and a rotary shaft 13d to open/close the outlet passage opening/closing door 9b. The rotary shaft 13a, the rotary shaft 13b, the rotary shaft 13c and the rotary shaft 13d are four rotary shafts which are independently rotatable. The rotary shaft 13a and the rotary shaft 13c are rotated as being synchronized. Further, the rotary shaft 13b and the rotary shaft 13d are rotated as being synchronized. Here, as illustrated in FIG. 7A, the four rotary shafts are rotated in a state of penetrating through the case 10a.

For improving sealing ability due to the inlet passage opening/closing door 8, it is preferable to stick lining on a peripheral border of the air inlet opening portion 3 at the top face 23 of the fragrance retention container 5. For improving sealing ability due to the outlet passage opening/closing door 9, it is preferable to stick lining on a peripheral border of the air outlet opening portion 4 at the top face 23 of the fragrance retention container 5.

Operation in the present embodiment will be described with reference to FIG. 8. As in FIG. 8A, the inlet passage opening/closing door 8a opens the air inlet opening portion 3a. The outlet passage opening/closing door 9a opens the air outlet opening portion 4a. The inlet passage opening/closing door 8b closes the air inlet opening portion 3b. The outlet passage opening/closing door 9b closes the air outlet opening portion 4b. A part of the air flow 19 inpoured to the inlet passage 6 from the inlet 15 flows into the accommodation space 2a from the air inlet opening portion 3a to be air flow 29a containing a fragrant ingredient as containing the fragrant ingredient of the fragrant agent 1a. The air flow 29a containing the fragrant ingredient flows to the outlet passage 7 through the air outlet opening portion 4a from the inside of the accommodation space 2a. Meanwhile, other air flow 30a which is not inpoured into the accommodation space 2a from the air inlet opening portion 3b flows to the outlet passage 7 through the shortcut hole 39 from the inlet passage 6. Air flow 20a being mixture of the air flow 30a with the air flow 29a containing the fragrant ingredient is supplied to the vehicle inside as being outpoured from the end part 31b of the outlet pipe 29 via the outlet 16, as illustrated in FIG. 5. Then, after predetermined time passes, the state shifts to that illustrated in FIG. 8B.

As illustrated in FIG. 8B, the inlet passage opening/closing door 8a closes the air inlet opening portion 3a. The outlet passage opening/closing door 9a closes the air outlet opening portion 4a. The inlet passage opening/closing door 8b closes the air inlet opening portion 3b. The outlet passage opening/closing door 9b closes the air outlet opening portion 4b. The air flow 19 inpoured to the inlet passage 6 from the inlet 15 is outpoured to the outlet passage 7 via the shortcut hole 39 formed at the partition plate 17, and then, is supplied to the vehicle inside after being outpoured from the end part 31b of the outlet pipe 29 as air flow 20b which does not contain any fragrant ingredient via the outlet 16, as illustrated in FIG. 5.

Here, the main body 10 includes the inlet passage opening/closing door 8 for each air inlet opening portion 3 and the outlet passage opening/closing door 9 for each air outlet opening portion 4 and is configured so that the inlet passage 6 and the outlet passage 7 become a directly connected passage when all of the air inlet opening portion 3 and the air outlet opening portion 4 are closed. By forming the inlet passage 6 and the outlet passage 7 to be the directly-connected passage when all of the air inlet opening portion 3 and the air outlet opening portion 4 are closed, the fragrant ingredient supplied when any of the air inlet opening portion 3 and the air outlet opening portion 4 is opened can be ejected owing to the air flow 20b which does not contain any fragrant ingredient. In this manner, supplying of the fragrant ingredient is stopped by sealing the air inlet opening portion 3 and the air outlet opening portion 4, so that the fragrant ingredient can be prevented from being wasted.

The cam 14 causes a mode in which all of the inlet passage opening/closing door 8 and the outlet passage opening/closing door 9 are closed to occur on the way when the inlet passage opening/closing door 8 and the outlet passage opening/closing door 9 corresponding to the air inlet opening portion 3 and the air outlet opening portion 4 of one accommodation space 2 are being switched from an opened state to a closed state and the inlet passage opening/closing door 8 and the outlet passage opening/closing door 9 corresponding to the air inlet opening portion 3 and the air outlet opening portion 4 of the other accommodation space 2 are being switched from an closed state to an opened state. By switching plural fragrant ingredients through the mode in which all of the inlet passage opening/closing door 8 and the outlet passage opening/closing door 9 are closed, the air flow 20b which does not contain a fragrant ingredient ejects the fragrant ingredient remaining in the outlet passage 7 and the outlet pipe 29. Accordingly, the plural fragrant ingredients are not mixed.

Subsequently, the state of FIG. 8B is shifted to the state illustrated in FIG. 8C after predetermined time passes. As in FIG. 8C, the inlet passage opening/closing door 8b opens the air inlet opening portion 3b. The outlet passage opening/closing door 9b opens the air outlet opening portion 4b. The inlet passage opening/closing door 8a closes the air inlet opening portion 3a. The outlet passage opening/closing door 9a closes the air outlet opening portion 4a. A part of the air flow 19 inpoured to the inlet passage 6 from the inlet 15 flows into the accommodation space 2b from the air inlet opening portion 3b to be air flow 29c containing a fragrant ingredient as containing the fragrant ingredient of the fragrant agent 1b. The air flow 29c containing the fragrant ingredient flows to the outlet passage 7 passing through the air outlet opening portion 4b from the inside of the accommodation space 2b. Meanwhile, other air flow 30c which is not inpoured into the accommodation space 2a from the air inlet opening portion 3a flows to the outlet passage 7 through the shortcut hole 39 from the inlet passage 6. Air flow 20c being mixture of the air flow 30c with the air flow 29c containing the fragrant ingredient is supplied to the vehicle inside as being outpoured from the end part 31b of the outlet pipe 29 via the outlet 16, as illustrated in FIG. 5. Then, after predetermined time passes, the state shifts to that illustrated in FIG. 8B. Thereafter, operation of FIGS. 8A, 8B and 8C is repeated.

Subsequently, with repeated to-and-fro operation in the order of A→B→C→B→A . . . , supplying to the vehicle inside is repeatedly performed in the order of the air flow 20a, the air flow 20b, the air flow 20c, the air flow 20b, the air flow 20a . . . . Alternatively, as needed basis, the air flow 20a and the air flow 20b are alternately supplied to the vehicle inside with repeated operation of A and B or the air flow 20b and the air flow 20c are alternately supplied to the vehicle inside with repeated operation of B and C. Here, the air flow 20 containing a fragrant ingredient illustrated in FIG. 5 includes the air flow 20a, the air flow 20b and the air flow 20c.

Figure 9A:
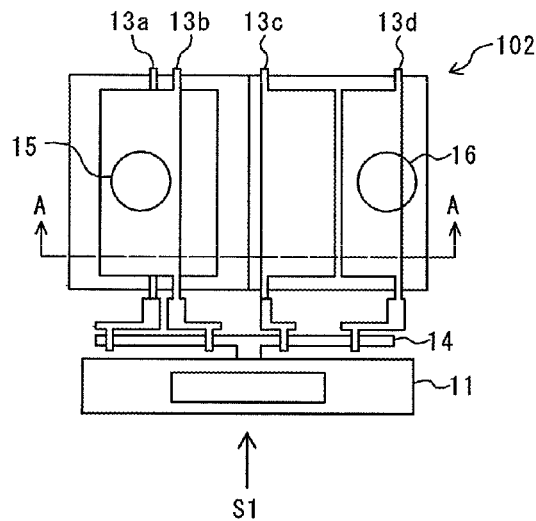
FIG. 9A is a plane view.
Figure 9C:
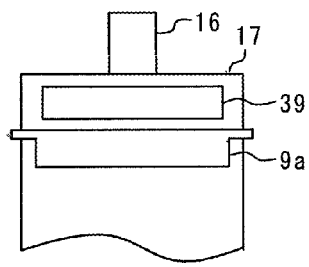
FIG. 9C is a sectional view at C-C of FIG. 9B viewing from direction S2.
Figure 9B:
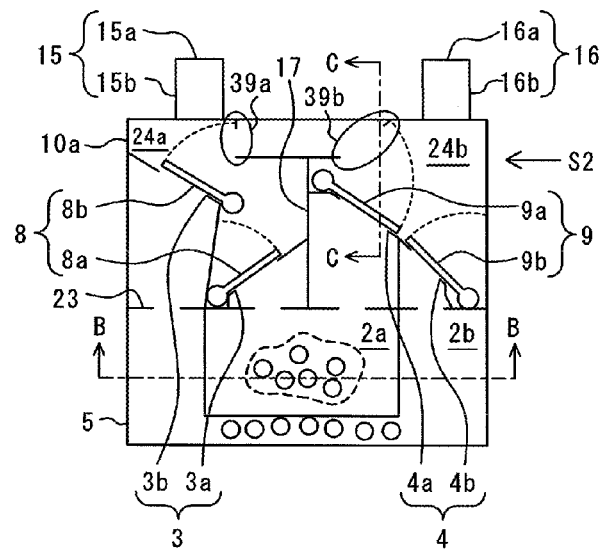
FIG. 9B is a sectional view at A-A of FIG. 9A viewing from direction S1.
Figure 9D:
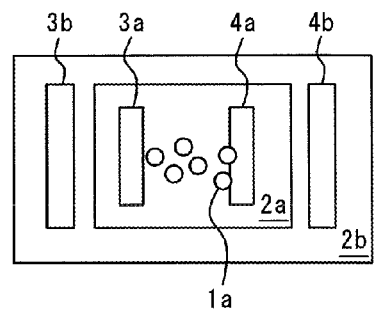
FIG. 9D is a sectional view at B-B of FIG. 9B.
Figure 10A:
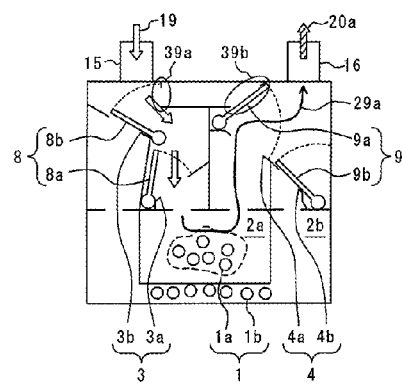
FIG. 10A illustrates a state that the fragrant ingredient of the fragrant agent 1a is supplied as one door being opened and the other door being closed.
Figure 10B:
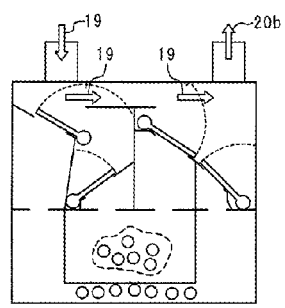
FIG. 10B illustrates a state that any fragrant ingredient is not supplied as all doors being closed.
Figure 10C:
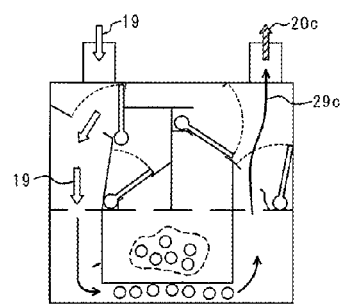
FIG. 10C illustrates a state that the fragrant ingredient of the fragrant agent 1b is supplied as the one door being closed and the other door being opened.

Next, a fragrance device 102 for a vehicle according to the third embodiment will be described with reference to FIGS. 9 and 10. FIG. 9 is a schematic sectional view of the fragrance device 102 for a vehicle according to the third embodiment. FIG. 9A is a plane view, FIG. 9B is a sectional view at A-A of FIG. 9A viewing from direction S1, FIG. 9C is a sectional view at C-C of FIG. 9B viewing from direction S2, and FIG. 9D is a sectional view at B-B of FIG. 9B. Further, FIG. 10 is an operational explanatory view of the fragrance device for a vehicle according to the third embodiment. FIG. 10A illustrates a state that the fragrant ingredient of the fragrant agent 1a is supplied as one door being opened and the other door being closed. FIG. 10B illustrates a state that any fragrant ingredient is not supplied as all doors being closed. FIG. 10C illustrates a state that the fragrant ingredient of the fragrant agent 1b is supplied as the one door being closed and the other door being opened.

The fragrance device 102 for a vehicle according to the third embodiment will be described with reference to FIG. 9. Here, since the fragrant agent 1 and the fragrance retention container 5 are similar to those of the first embodiment, description thereof is not repeated here.

As illustrated in FIG. 9, in the fragrance device 102 for a vehicle according to the third embodiment, the fragrance retention container 5 is provided with respective pluralities of fragrant agents 1, air inlet opening portions 3, air outlet opening portions 4, inlet passage opening/closing doors 8 and outlet passage opening/closing doors 9. The inlet passage opening/closing doors 8 and the outlet passage opening/closing doors 9 are attached respectively to separate rotary shafts 13 at positions where opening/closing of the air inlet opening portions 3 and the air outlet opening portions 4 are synchronized. The main body 10 includes a shortcut hole 39 which connects the inlet passage 6 and the outlet passage 7. Here, it is preferable that any one of the inlet passage opening/closing doors 8 closes an inlet 39a of the shortcut hole 39 when the air inlet opening portion 3 is opened while any one of the outlet passage opening/closing doors 9 closes an outlet 39b of the shortcut hole 39 when the air outlet opening portion 4 is opened.

As illustrated in FIG. 9, the inlet 15 having the inlet opening portion 15a at the distal end of the inlet pipe 15b and the outlet 16 having the outlet opening portion 16a at the distal end of the outlet pipe 16b are arranged at the top face of the case 10a of the main body 10. The case 10a is located above the fragrance retention container 5. The bottom face of the case 10a is formed open and is closed with the top face 23 of the fragrance retention container 5. The partition plate 17 in the case 10a is arranged to divide the space in the case 10a into two spaces of the inlet side space 24a and the outlet side space 24b.

As illustrated in FIG. 9, the case 10a of the main body 10 includes the inlet passage opening/closing door 8b to open/seal the air inlet opening portion 3b, the outlet passage opening/closing door 9b to open/seal the air outlet opening portion 4b, the inlet passage opening/closing door 8a to open/seal the air inlet opening portion 3a, and the outlet passage opening/closing door 9a to open/seal the air outlet opening portion 4a. The inlet passage opening/closing door 8a may be formed as any opening/closing type in any shape as long as the air inlet opening portion 3a can be opened and sealed. The inlet passage opening/closing door 8b may be formed as any opening/closing type in any shape as long as the air inlet opening portion 3b and the inlet 39a of the shortcut hole can be opened and sealed. The outlet passage opening/closing door 9a may be formed as any opening/closing type in any shape as long as the air outlet opening portion 4a and the outlet 39b of the shortcut hole can be opened and sealed. The outlet passage opening/closing door 9b may be formed as any opening/closing type in any shape as long as the air outlet opening portion 4b can be opened and sealed.

The case 10a further includes the rotary shaft 13a to open/close the inlet passage opening/closing door 8a, the rotary shaft 13c to open/close the outlet passage opening/closing door 9a, the rotary shaft 13b to open/close the inlet passage opening/closing door 8b, and the rotary shaft 13d to open/close the outlet passage opening/closing door 9b. The rotary shaft 13a, the rotary shaft 13b, the rotary shaft 13c and the rotary shaft 13d are four rotary shafts which are independently rotatable. The rotary shaft 13a and the rotary shaft 13c are rotated as being synchronized. Further, the rotary shaft 13b and the rotary shaft 13d are rotated as being synchronized. Here, as illustrated in FIG. 9A, the four rotary shafts are rotated in a state of penetrating through the case 10a.

The shortcut hole 39 is formed at the partition plate 17 and is provided with the inlet 39a of the shortcut hole and the outlet 39b of the shortcut hole. The shortcut hole 39 is configured so that the outlet 39b of the shortcut hole 39 is closed by the outlet passage opening/closing door 9a and the inlet 39a of the shortcut hole 39 is closed by the inlet passage opening/closing door 8b. Here, the inlet passage 6 (not illustrated) is configured with the inlet pipe 15b, the case 10a, the partition plate 17 and the container top face 23. The outlet passage 7 (not illustrated) is constituted with the container top face 23, the partition plate 17, the case 10a and the outlet pipe 16b.

For improving sealing ability due to the inlet passage opening/closing door 8, it is preferable to stick lining on a peripheral border of the air inlet opening portion 3 at the top face 23 of the fragrance retention container 5. For improving sealing ability due to the outlet passage opening/closing door 9, it is preferable to stick lining on a peripheral border of the air outlet opening portion 4 at the top face 23 of the fragrance retention container 5. In addition, it is preferable to stick lining on a peripheral border of the outlet 39b of the shortcut hole 39 for improving sealing ability due to outlet passage opening/closing door 9a. It is preferable to stick lining on a peripheral border of the inlet 39a of the shortcut hole 39 for improving sealing ability due to inlet passage opening/closing door 8b.

Operation in the present embodiment will be described with reference to FIG. 10. As in FIG. 10A, the inlet passage opening/closing door 8a opens the air inlet opening portion 3a. The outlet passage opening/closing door 9a opens the air outlet opening portion 4a. The inlet passage opening/closing door 8b closes the air inlet opening portion 3b. The outlet passage opening/closing door 9b closes the air outlet opening portion 4b. At the same time, the outlet passage opening/closing door 9a closes the outlet 39b of the shortcut hole 39. The air flow 19 inpoured to the inlet passage 6 from the inlet 15 flows into the accommodation space 2a from the air inlet opening portion 3a to be air flow 29a containing a fragrant ingredient as containing the fragrant ingredient of the fragrant agent 1a. The air flow 29a containing the fragrant ingredient flows to the outlet passage 7 through the air outlet opening portion 4a from the inside of the accommodation space 2a. With the above configuration, all of the air flow 19 can be inpoured to the accommodation space 2a and the fragrant ingredient can be supplied by effectively utilizing the air flow 19. The air flow 29a containing the fragrant ingredient is supplied to the vehicle inside as being outpoured from the end part 31b of the outlet pipe 29 via the outlet 16 as the air flow 20a, as illustrated in FIG. 5. Then, after predetermined time passes, the state shifts to that illustrated in FIG. 10B.

As illustrated in FIG. 10B, the inlet passage opening/closing door 8a closes the air inlet opening portion 3a. The outlet passage opening/closing door 9a closes the air outlet opening portion 4a. The inlet passage opening/closing door 8b closes the air inlet opening portion 3b. The outlet passage opening/closing door 9b closes the air outlet opening portion 4b. At the same time, the outlet passage opening/closing door 9a opens the outlet 39b of the shortcut hole 39. The air flow 19 inpoured to the inlet passage 6 from the inlet 15 is outpoured to the outlet passage 7 via the outlet 39b of the shortcut hole 39 from the inlet 39a of the shortcut hole 39 formed at the partition plate 17, and then, is supplied to the vehicle inside after being outpoured from the end part 31b of the outlet pipe 29 as air flow 20b which does not contain any fragrant ingredient via the outlet 16, as illustrated in FIG. 5. With the above configuration, the fragrant ingredient remaining between the outlet passage 7 and the outlet pipe 29 can be ejected when switching fragrant ingredients.

Here, the main body 10 includes the inlet passage opening/closing door 8 for each air inlet opening portion 3 and the outlet passage opening/closing door 9 for each air outlet opening portion 4 and is configured so that the inlet passage 6 and the outlet passage 7 become a directly connected passage when all of the air inlet opening portion 3 and the air outlet opening portion 4 are closed. By forming the inlet passage 6 and the outlet passage 7 to be the directly-connected passage when all of the air inlet opening portion 3 and the air outlet opening portion 4 are closed, the fragrant ingredient supplied when any of the air inlet opening portion 3 and the air outlet opening portion 4 is opened can be ejected owing to the air flow 20b which does not contain any fragrant ingredient. In this manner, supplying of the fragrant ingredient is stopped by sealing the air inlet opening portion 3 and the air outlet opening portion 4, so that the fragrant ingredient can be prevented from being wasted.

The cam 14 causes a mode in which all of the inlet passage opening/closing door 8 and the outlet passage opening/closing door 9 are closed to occur on the way when the inlet passage opening/closing door 8 and the outlet passage opening/closing door 9 corresponding to the air inlet opening portion 3 and the air outlet opening portion 4 of one accommodation space 2 are being switched from an opened state to a closed state and the inlet passage opening/closing door 8 and the outlet passage opening/closing door 9 corresponding to the air inlet opening portion 3 and the air outlet opening portion 4 of the other accommodation space 2 are being switched from an closed state to an opened state. By switching plural fragrant ingredients through the mode in which all of the inlet passage opening/closing door 8 and the outlet passage opening/closing door 9 are closed, the air flow 20b which does not contain a fragrant ingredient ejects the fragrant ingredient remaining in the outlet passage 7 and the outlet pipe 29. Accordingly, the plural fragrant ingredients are not mixed.

Subsequently, the state of FIG. 10B is shifted to the state illustrated in FIG. 10C after predetermined time passes. As in FIG. 10C, the inlet passage opening/closing door 8b opens the air inlet opening portion 3b. The outlet passage opening/closing door 9b opens the air outlet opening portion 4b. The inlet passage opening/closing door 8a closes the air inlet opening portion 3a. The outlet passage opening/closing door 9a closes the air outlet opening portion 4a. At the same time, the inlet passage opening/closing door 8b closes the inlet 39a of the shortcut hole 39. The air flow 19 inpoured to the inlet passage 6 from the inlet 15 flows into the accommodation space 2b from the air inlet opening portion 3b to be air flow 29c containing a fragrant ingredient as containing the fragrant ingredient of the fragrant agent 1b. The air flow 29c containing the fragrant ingredient flows to the outlet passage 7 passing through the air outlet opening portion 4b from the inside of the accommodation space 2b. With the above configuration, all of the air flow 19 can be inpoured to the accommodation space 2b and the fragrant ingredient can be supplied by effectively utilizing the air flow 19. The air flow 29c containing the fragrant ingredient is supplied to the vehicle inside as being outpoured from the end part 31b of the outlet pipe 29 via the outlet 16 as the air flow 20a, as illustrated in FIG. 5. Then, after predetermined time passes, the state shifts to that illustrated in FIG. 10B.

Subsequently, with repeated to-and-fro operation in the order of A→B→C→B→A . . . , supplying to the vehicle inside is repeatedly performed in the order of the air flow 20a, the air flow 20b, the air flow 20c, the air flow 20b, the air flow 20a . . . . Alternatively, as needed basis, the air flow 20a and the air flow 20b are alternately supplied to the vehicle inside with repeated operation of A and B or the air flow 20b and the air flow 20c are alternately supplied to the vehicle inside with repeated operation of B and C. Here, the air flow 20 containing a fragrant ingredient illustrated in FIG. 5 includes the air flow 20a, the air flow 20b and the air flow 20c.

Next, an aspect with accommodation spaces of which volume is different for each fragrant agent will be described in detail. The fragrance device 100 for a vehicle according to the first embodiment will be described with reference to FIGS. 1 to 5 and FIG. 11. FIG. 11 is a schematic view illustrating plural accommodation spaces respectively having a different volume in the fragrance retention container. FIG. 11A illustrates a state of being divided by an intra-container partition plate. FIG. 11B illustrates another state of being divided by an intra-container partition plate. FIG. 11C illustrates a state that a different volume is obtained by accommodating a dummy member in one accommodation space of accommodation spaces having the same volume.

As illustrated in FIGS. 1 to 3 and FIG. 11, the fragrance device 100 for a vehicle according to the first embodiment includes plural accommodation spaces 2 for accommodating the fragrant agents 1, the fragrance retention container 5 having the air inlet opening portion 3 and the air outlet opening portion 4 which are arranged for each accommodation space 2, the main body 10 to which the fragrance retention container 5 is attached having the inlet passage opening/closing doors 8 which respectively perform opening/closing of each air inlet opening portion 3 and the outlet passage opening/closing doors 9 which respectively perform opening/closing of each air outlet opening portion 4. In the fragrance device 100 for a vehicle capable of intermittently supplying fragrant ingredients of the fragrant agents 1 to the vehicle inside as being contained in air flow, volumes of the accommodation spaces 2 respectively differ for each fragrant agent 1.

As illustrated in FIG. 11, regarding the accommodation space 2a to accommodate the fragrant agent 1a and the accommodation space 2b to accommodate the fragrant agent 1b, it is preferable that volumes of the accommodation space 2a and the accommodation space 2b are set to be different to each other for each fragrant agent. With the above configuration of the accommodation spaces 2, respective accumulation amounts of the fragrant ingredient of the fragrant agent 1a accommodated in the accommodation space 2a and the fragrant ingredient of the fragrant agent 1b accommodated in the accommodation space 2b can be different to each other. Since the fragrance device 100 for a vehicle can supply the accumulated fragrant ingredient to a vehicle inside as a supply amount for one time, it is not required to arrange control means which corresponds to the fragrant ingredient of the fragrant agent 1a accommodated in the accommodation space 2a or the fragrant ingredient of the fragrant agent 1b accommodated in the accommodation space 2b.

Specifically, it is preferable that the volumes are varied by a partitioning ratio of the accommodation space 2 with the intra-container partition plate 22. As illustrated in FIG. 11A, the accommodation space 2 is partitioned into the accommodation space 2a and the accommodation space 2b of which volumes are different to each other by placing the intra-container partition plate 22 in the fragrance retention container 5 so that $t_1$ and $t_2$ are set to be different length to each other. In the case that combination of the fragrant agents 1 is not changed, the accommodation space 2a and the accommodation space 2b can be structured simply and inexpensively by forming the intra-container partition plate 22 as previously setting the volumes of the accommodation space 2a and the accommodation space 2b. Here, as illustrated in FIG. 11B, it is also possible that the intra-container partition plate 22 may be formed in a curved-shape to ensure required volumes corresponding to kinds of the fragrant agents 1 as long as the accommodation space 2 can be divided into the accommodation space 2a and the accommodation space 2b.

As another specific example, it is preferable that the volume of the accommodation space 2 is varied owing to a volume of a dummy member 44 to be accommodated in the accommodation space. As illustrated in FIG. 11C, the accommodation space 2 is divided into the accommodation space 2a and the accommodation space 2b to have the same volume by placing the intra-container partition plate 22 in the fragrance retention container 5 so that $t_1$ and $t_2$ are equaled. Then, the dummy member 44 is accommodated in the accommodation space 2a of which volume is desired to be decreased. The volume of the accommodation space 2a is decreased owing to increase of the volume of the dummy member 44. Since the volume of the other accommodation space 2b is not varied, the volume of the accommodation space 2a and the volume of the accommodation space 2b are to be different. In the case that combination of the fragrant agents 1 is to be changed, the volume of the accommodation space 2a or the volume of the accommodation space 2b can be easily changed by accommodating the dummy member 44 in the accommodation space 2a or the accommodation space 2b as appropriately selecting corresponding to the kind of the fragrant agent 1 to be accommodated. Accordingly, it is possible to support combination change of the fragrant agents 1 for shipping the fragrance device 100 for a vehicle by varying the volume of the dummy member 44 to be accommodated in each accommodation space 2 by utilizing a plurality of the fragrance retention containers 5 having the accommodation spaces 2 of the same volume. Further, when the combination of the fragrant agents 1 is replaced with another combination, it is possible to support the combination change of the fragrant agents 1 by changing the volume of the dummy member 44 which is to be accommodated in each accommodation space 2. Here, the dividing means of the accommodation space 2 illustrated in FIGS. 11A to 11C can be used as being respectively combined.

Further, it is preferable that the fragrant agents 1 adopt the fragrant agent 1b which is large and heavy and the fragrant agent 1a which is smaller and lighter than the fragrant agent 1b and that the fragrant agent 1b is sized as being capable of being accommodated in the large-volume accommodation space 2b and as being incapable of being accommodated in the small-volume accommodation space 2a while the fragrant agent 1a is sized as being capable of being accommodated in the accommodation space 2a. As illustrated in FIG. 11, it is also possible to adjust the size and weight of the fragrant agents 1 with bags 43. Owing to weight difference, it is possible to easily discriminate between kinds of the fragrant agent 1a and the fragrant agent 1b. Further, owing to dimension difference, it is possible to easily discriminate among combinations of the kinds of the fragrant agent 1a and the fragrant agent 1b with the accommodation space 2a and the accommodation space 2b for required accommodation. Either or both of dimensions and weight of the fragrant agent 1a and the fragrant agent 1b may be set different to each other. Further, it is also possible to vary saturated vapor pressure as dissolving a fragrant ingredient in solvent. Accordingly, it is possible to adjust the amount of the fragrant ingredient to be pervaded. For example, dipropylene glycol, methoxymethyl butanol and liquid paraffin may be adopted as the solvent.

Further, it is preferable that the fragrant agents 1 adopt the fragrant agent 1b having a large detection threshold value of the fragrant ingredient and the fragrant agent 1a having a smaller detection threshold value than that of the fragrant agent 1b and that the fragrant agent 1b having the large detection threshold value is to be accommodated in the large accommodation space 2b and the fragrant agent 1a having the small detection threshold value is to be accommodated in the smaller accommodation space 2a than the large accommodation space 2b. Here, the threshold value denotes the minimum stimulant amount at which fragrance can be detected by a human sensory organ. Then, the detection threshold value denotes concentration of a fragrant ingredient to be capable of being detected. The smaller detection threshold value indicates that fragrance can be detected with the less fragrant ingredient. The fragrant ingredient of the fragrant agent 1a having the small detection threshold value is capable of strengthening odor intensity in the vehicle inside even with a little supplying amount. Accordingly, the odor intensity in the vehicle inside can be prevented from being strengthened beyond necessity as being supplied relatively less by being accumulated in the small accommodation space 2a only in a small amount. On the other hand, the fragrant ingredient of the fragrant agent 1b having the large detection threshold value cannot strengthen the odor intensity in the vehicle inside unless a large amount is supplied. Accordingly, the odor intensity in the vehicle inside can be sufficiently strengthened as being supplied relatively more by being accumulated in the large accommodation space 2b in a large amount. In this manner, the fragrance device 100 for a vehicle can supply fragrant ingredients respectively at appropriate odor intensity to a vehicle inside whether a detection threshold value of a fragrant ingredient is large or small.

Further, it is preferable that the fragrant agents 1 adopt the fragrant agent 1b having a large evaporation rate of the fragrant ingredient and the fragrant agent 1a having a smaller evaporation rate than that of the fragrant agent 1b and that (I) the fragrant agent 1b having the large evaporation rate is accommodated in the small accommodation space 2a and the fragrant agent 1a having the small evaporation rate is accommodated in the accommodation space 2b which is larger than the small accommodation space 2a or (II) the fragrant agent 1b having the large evaporation rate is accommodated in the large accommodation space 2b and the fragrant agent 1a having the small evaporation rate is accommodated in the accommodation space 2a which is smaller than the large accommodation space 2b. When being configured as (I), the fragrant agent 1b having the large evaporation rate can be prevented from causing excessively strengthened odor intensity due to volatilization of the fragrant ingredient beyond necessity after reaching saturated vapor pressure as being volatized in the small accommodation space 2a. Meanwhile, the fragrant agent 1a having the small evaporation rate can ensure a sufficient accumulation amount in the large accommodation space 2b. Accordingly, since the fragrant agent 1b having the large evaporation rate is accommodated in the small accommodation space 2a, the accumulation amount thereof can be matched to the accumulation amount of the fragrant agent 1 having the small evaporation rate. Consequently, the fragrance device 100 for a vehicle can supply fragrant ingredients to the vehicle inside as being adjusted at constant odor intensity regardless of the evaporation rates of the fragrant agent 1a and the fragrant agent 1b. On the other hand, when being configured as (II), it is possible to reduce difference of the time until the fragrant ingredient reaches the saturated vapor pressure as being pervaded in the accommodation space (i.e., the time until accumulation is completed) between the fragrant ingredient of the fragrant agent 1a having the small evaporation rate and the fragrant ingredient of the fragrant agent 1b having the large evaporation rate even when the accommodation volumes are set to be different. Accordingly, it is possible to prevent the time until accumulation of the fragrant ingredient having the small evaporation rate is completed from being prolonged, so that designing of control to intermittently supply fragrant ingredients can be facilitated.

As illustrated in FIG. 3, the inlet passage opening/closing door 8b and the outlet passage opening/closing door 9b are attached to the single rotary shaft 12b at positions where opening/closing of the air inlet opening portion 3b and the air outlet opening portion 4b is synchronized. That is, the inlet passage opening/closing door 8a and the outlet passage opening/closing door 9a open and close the air inlet opening portion 3a and the air outlet opening portion 4a in synchronization with each other. The inlet passage opening/closing door 8b and the outlet passage opening/closing door 9b open and close the air inlet opening portion 3b and the air outlet opening portion 4b in synchronization with each other. With the above configuration, it is possible to accumulate the fragrant ingredient of the fragrant agent 1a accommodated in the accommodation space 2a and to accumulate the fragrant ingredient of the fragrant agent 1b accommodated in the accommodation space 2b.

Here, when the trajectory groove 21 is set to be shaped so that all of the inlet passage opening/closing door 8 and the outlet passage opening/closing door 9 are not closed, it is also possible to perform alternate operation that either (1) the inlet passage opening/closing door 8a and the outlet passage opening/closing door 9a or (2) the inlet passage opening/closing door 8b and the outlet passage opening/closing door 9b is constantly opened.

The operation of the fragrance device 100 for a vehicle in FIG. 6 is as described above.

Figure 12A:
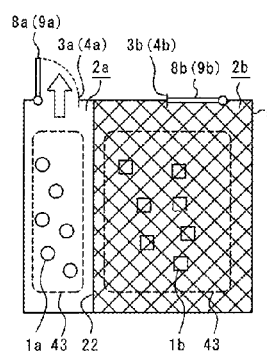
FIG. 12A illustrates a state that the accommodation space 2a is opened and the accommodation space 2b is closed.
Figure 12B:
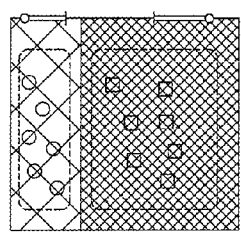
FIG. 12B illustrates a state that the accommodation space 2a is closed and the accommodation space 2b is closed.
Figure 12C:
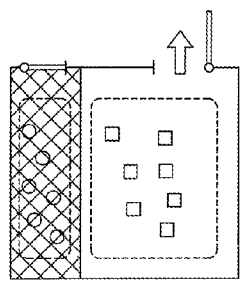
FIG. 12C illustrates a state that the accommodation space 2a is closed and the accommodation space 2b is opened.
Figure 12D:
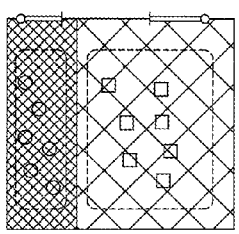
FIG. 12D illustrates a state that the accommodation space 2a is closed and the accommodation space 2b is closed. Here, higher concentration of the fragrant ingredient is indicated by a darker hatched portion.

Next, operation of accumulating and supplying of the fragrance device 100 for a vehicle will be described with reference to FIG. 12. FIG. 12 is a schematic sectional view illustrating the operation of accumulating and supplying of the fragrance device 100 for a vehicle according to the present invention. FIG. 12A illustrates a state that the accommodation space 2a is opened and the accommodation space 2b is closed. FIG. 12B illustrates a state that the accommodation space 2a is closed and the accommodation space 2b is closed. FIG. 12C illustrates a state that the accommodation space 2a is closed and the accommodation space 2b is opened. FIG. 12D illustrates a state that the accommodation space 2a is closed and the accommodation space 2b is closed. Here, higher concentration of the fragrant ingredient is indicated by a darker hatched portion.

As illustrated in FIG. 12A, the accommodation space 2a is opened and the fragrant ingredient of the fragrant agent 1a of which accumulation is completed in the accommodation space 2a is supplied accordingly. Concurrently, the accommodation space 2b is maintained in a closed state and the fragrant ingredient of the fragrant agent 1b is gradually volatilized. Then, after predetermined time passes, the state shifts to that illustrated in FIG. 12B.

As illustrated in FIG. 12B, the accommodation space 2a is closed and the fragrant ingredient of the fragrant agent 1a starts to be accumulated in the accommodation space 2a. Concurrently, the accommodation space 2b is maintained in a closed state, so that the fragrant ingredient of the fragrant agent 1b is pervaded and accumulation is completed. Then, after predetermined time passes, the state shifts to that illustrated in FIG. 12C.

As illustrated in FIG. 12C, the accommodation space 2a is maintained in a closed state and the fragrant ingredient of the fragrant agent 1a is gradually volatilized. Concurrently, the accommodation space 2b is opened and the fragrant ingredient of the fragrant agent 1b of which accumulation is completed in the accommodation space 2b is supplied accordingly. Then, after predetermined time passes, the state shifts to that illustrated in FIG. 12D.

As illustrated in FIG. 12D, the accommodation space 2a is maintained in the closed state and the fragrant ingredient of the fragrant agent 1a is pervaded and accumulation is completed. Concurrently, the accommodation space 2b is closed and the fragrant ingredient of the fragrant agent 1b starts to be accumulated in the accommodation space 2b. Then, after predetermined time passes, the state shifts to that illustrated in FIG. 12A.

Subsequently, with repeated operation in the order of A→B→C→D→A..., the fragrant ingredient of the fragrant agent 1a and the fragrant ingredient of the fragrant agent 1b are supplied to the vehicle inside alternately and intermittently.

Similarly, in the fragrance device 101 for a vehicle according to the second embodiment illustrated in FIGS. 7 and 8, it is possible to adopt the aspect with accommodation spaces of which volumes are different for each fragrant agent. Here, when the inlet passage opening/closing door 8a and the outlet passage opening/closing door 9a close the air inlet opening portion 3a and the air outlet opening portion 4a in synchronization with each other, the fragrant ingredient of the fragrant agent 1a can be accumulated in the accommodation space 2a. When the inlet passage opening/closing door 8b and the outlet passage opening/closing door 9b close the air inlet opening portion 3b and the air outlet opening portion 4b in synchronization with each other, the fragrant ingredient of the fragrant agent 1b can be accumulated in the accommodation space 2b.

The operation of the fragrance device 101 for a vehicle in FIG. 8 is as described above.

Figure 13A:
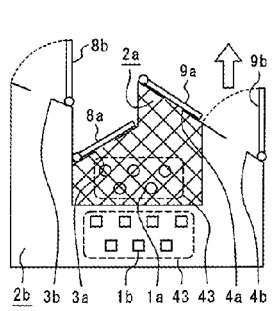
FIG. 13A illustrates a state that the accommodation space 2a is closed and the accommodation space 2b is opened.
Figure 13B:
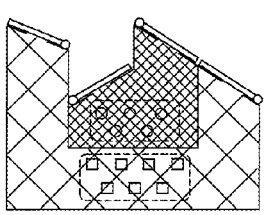
FIG. 13B illustrates a state that the accommodation space 2a is closed and the accommodation space 2b is closed.
Figure 13C:
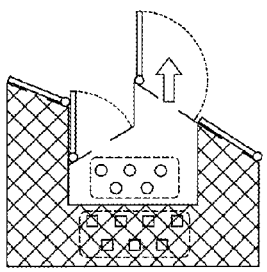
FIG 13C illustrates a state that the accommodation space 2a is opened and the accommodation space 2b is closed.
Figure 13D:
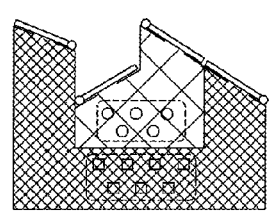
FIG. 13D illustrates a state that the accommodation space 2a is closed and the accommodation space 2b is closed. Here, higher concentration of the fragrant ingredient is indicated by a darker hatched portion.

Next, operation of accumulating and supplying of the fragrance device 101 for a vehicle will be described with reference to FIG. 13. FIG. 13 is a schematic sectional view illustrating the operation of accumulating and supplying of the fragrance device 101 for a vehicle according to the present invention. FIG. 13A illustrates a state that the accommodation space 2a is closed and the accommodation space 2b is opened. FIG. 13B illustrates a state that the accommodation space 2a is closed and the accommodation space 2b is closed. FIG. 13C illustrates a state that the accommodation space 2a is opened and the accommodation space 2b is closed. FIG. 13D illustrates a state that the accommodation space 2a is closed and the accommodation space 2b is closed. Here, higher concentration of the fragrant ingredient is indicated by a darker hatched portion.

As illustrated in FIG. 13A, the accommodation space 2a is maintained in a closed state and the fragrant ingredient of the fragrant agent 1a is gradually volatilized. Concurrently, the accommodation space 2b is opened and the fragrant ingredient of the fragrant agent 1b of which accumulation is completed in the accommodation space 2b is supplied accordingly. Then, after predetermined time passes, the state shifts to that illustrated in FIG. 13B.

As illustrated in FIG. 13B, the accommodation space 2a is maintained in the closed state and the fragrant ingredient of the fragrant agent 1a is pervaded and accumulation is completed. Concurrently, the accommodation space 2b is closed and the fragrant ingredient of the fragrant agent 1a starts to be accumulated in the accommodation space 2b. Then, after predetermined time passes, the state shifts to that illustrated in FIG. 13C.

As illustrated in FIG. 13C, the accommodation space 2a is opened and the fragrant ingredient of the fragrant agent 1a of which accumulation is completed in the accommodation space 2a is supplied accordingly. Concurrently, the accommodation space 2b is maintained in the closed state and the fragrant ingredient of the fragrant agent 1b is gradually volatilized. Then, after predetermined time passes, the state shifts to that illustrated in FIG. 13D.

As illustrated in FIG. 13D, the accommodation space 2a is closed and the fragrant ingredient of the fragrant agent 1a starts to be accumulated in the accommodation space 2a. Concurrently, the accommodation space 2b is maintained in the closed state, so that the fragrant ingredient of the fragrant agent 1b is pervaded and accumulation is completed. Then, after predetermined time passes, the state shifts to that illustrated in FIG. 13A.

Subsequently, with repeated operation in the order of A→B→C→D→A..., the fragrant ingredient of the fragrant agent 1a and the fragrant ingredient of the fragrant agent 1b are supplied to the vehicle inside alternately and intermittently.

Similarly, in the fragrance device 102 for a vehicle according to the third embodiment illustrated in FIGS. 9 and 10, it is possible to adopt the aspect with accommodation spaces of which volumes are different for each fragrant agent. Here, when the inlet passage opening/closing door 8a and the outlet passage opening/closing door 9a close the air inlet opening portion 3a and the air outlet opening portion 4a in synchronization with each other, the fragrant ingredient of the fragrant agent 1a can be accumulated in the accommodation space 2a. When the inlet passage opening/closing door 8b and the outlet passage opening/closing door 9b close the air inlet opening portion 3b and the air outlet opening portion 4b in synchronization with each other, the fragrant ingredient of the fragrant agent 1b can be accumulated in the accommodation space 2b.

Here, since operation of accumulating and supplying of the fragrance device 102 for a vehicle is similar to the above operation of accumulating and supplying of the fragrance device 101 for a vehicle, description thereof will be not repeated here.

Next, a sealing component will be described in detail. A sealing component and the fragrance device for a vehicle incorporating the sealing component according to the first embodiment will be described with reference to FIG. 2 and FIGS. 14 to 17. The fragrance device 100 for a vehicle is provided with the fragrance retention container 5 including the accommodation space 2 (2a, 2b) which accommodates the fragrance agent 1 and a container opening portion 60 (3a, 3b, 4a, 4b), and the main body 10 including a main body internal space 24 (24a, 24b) to be an air flow passage 63 (6, 7), a main body opening portion 61, and a passage opening/closing door 62 (8a, 8b, 9a, 9b) which opens and closes the main body opening portion 61 from the inside. The fragrance retention container 5 is attached to the main body 10 in a state that the accommodation space 2 (2a, 2b) is communicated with the main body internal space 24 (24a, 24b) via the container opening portion 60 and the main body opening portion 61, so that the fragrant ingredient of the fragrant agent 1 is added to air flow of the air-conditioning device. Here, the main body opening portion 61 is illustrated in FIG. 17. The sealing component 50 made of elastic material is used for the fragrance device 100 for a vehicle as being sandwiched between mating faces of the fragrance retention container 5 and the main body 10. The sealing component 50 includes a hole portion 53 which causes communication between the accommodation space 2 (2a, 2b) and the main body internal space 24 (24a, 24b), a door side pressure-contact portion 54 of which opening portion 56 at one end side of the hole portion 53 is closed as being pressure-contacted with a door face when the passage opening/closing door 62 is closed as the opening portion 56 at the one end side being arranged in the main body internal space 24 (24a, 24b), and a container side pressure-contact portion 55 which seals the container opening portion 60 as being sandwiched and pressure-contacted by the fragrance retention container 5 and the main body 10 while an opening portion 57 at the other end side of the hole portion 53 is arranged between the fragrance retention container 5 and the main body 10. Then, the door side pressure-contact portion 54 and the container side pressure-contact portion 55 are integrally formed.

Figure 14:
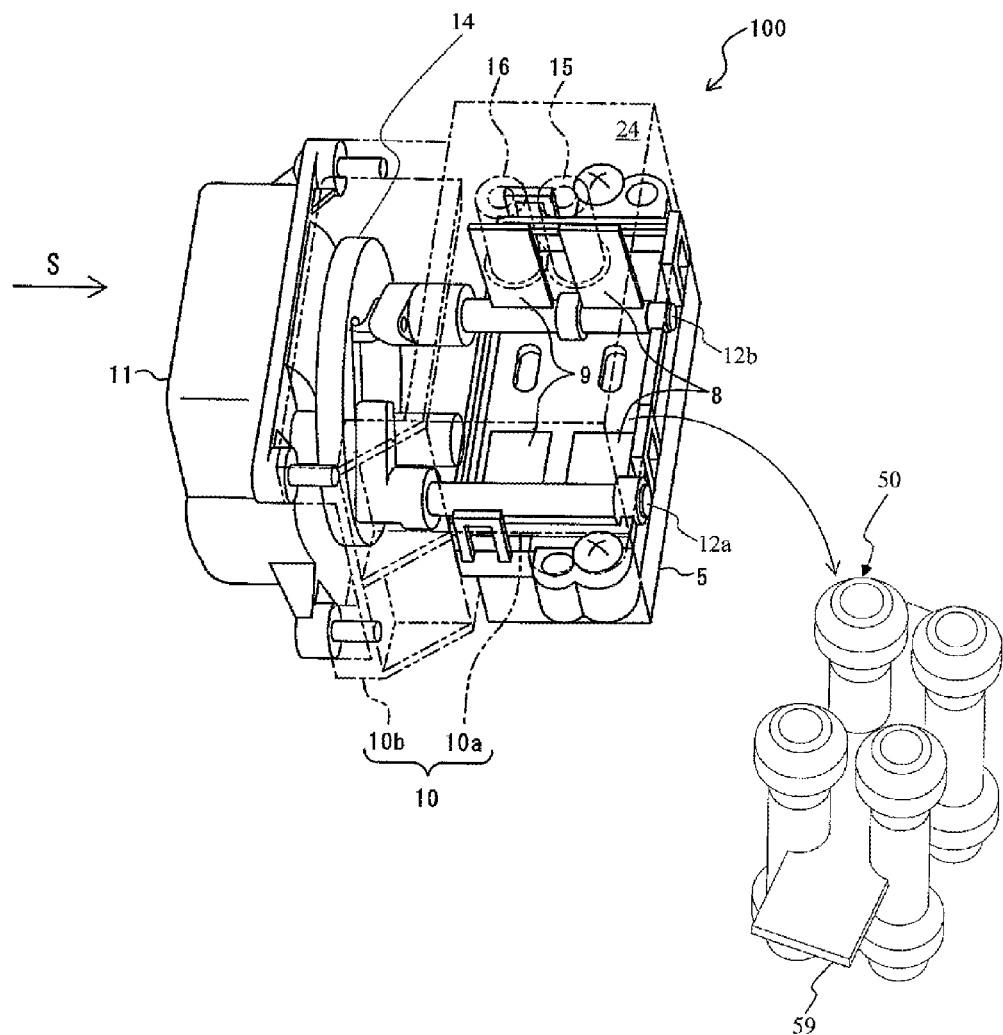
FIG. 14 is a perspective view of a sealing component according to the first embodiment and the fragrance device for a vehicle incorporating the component.
Figure 15:
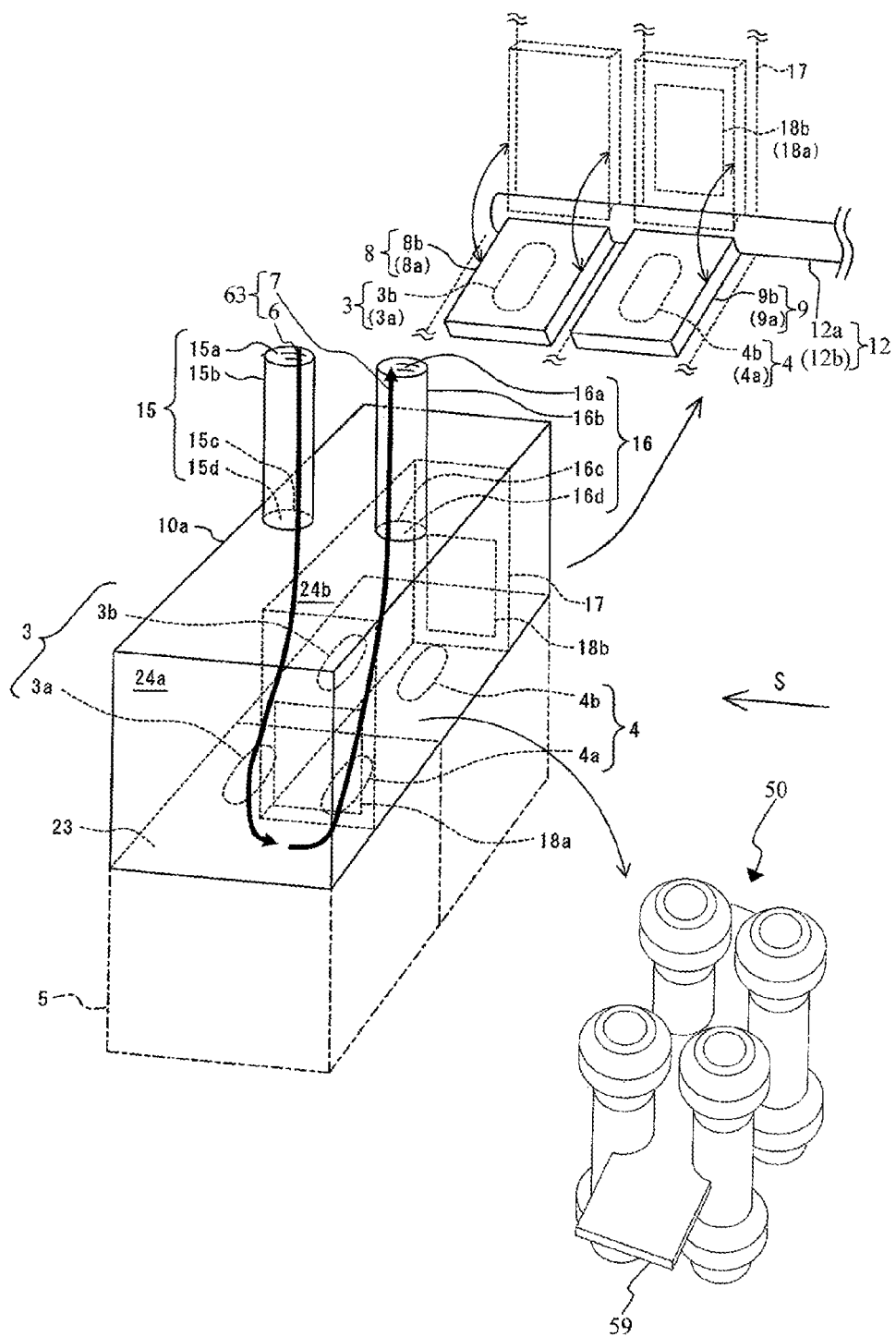
FIG. 15 is a schematic view of the main body in FIG. 14 and the sealing component according to the first embodiment to be incorporated therein.

Here, as illustrated in FIGS. 15 and 17, the container opening portion 60 includes the air inlet opening portion 3 and the air outlet opening portion 4. The passage opening/closing door 62 includes the inlet passage opening/closing door 8 and the outlet passage opening/closing door 9. The air flow passage 63 includes the inlet passage 6 and the outlet passage 7. The main body internal space 24 includes the inlet side space 24a and the outlet side space 24b. The main body 10 to which the fragrance retention container 5 is attached includes the inlet passage 6 to inpour air to the air inlet opening portion 3, the outlet passage 7 to outpour air containing the fragrant ingredient from the air outlet opening portion 4, the inlet passage opening/closing door 8 to open/close the air inlet opening portion 3, and the outlet passage opening/closing door 9 to open/close the air outlet opening portion 4. Further, the single actuator 11 which is fixed and a single cam 14 (illustrated in FIG. 14) which is connected to the actuator 11 to rotationally drive the rotary shaft 12 of the inlet passage opening/closing door 8 and the rotary shaft 12 of the outlet passage opening/closing door 9 are disposed.

As illustrated in FIG. 15, the inlet passage 6 is constituted with the inlet pipe 15b, the case 10a, the partition plate 17 and a main body bottom 64 which is illustrated in FIG. 17. The outlet passage 7 is constituted with the outlet pipe 16b, the case 10a, the partition plate 17 and the main body bottom 64. Further, the inlet 15 having the inlet opening portion 15a at the distal end of the inlet pipe 15b and the outlet 16 having the outlet opening portion 16a at the distal end of the outlet pipe 16b are arranged at the top face of the case 10a of the main body 10. Then, as illustrated in FIG. 17, the main body bottom 64 includes the same number of main body opening portions 61 as the number of the container opening portions 60.

As illustrated in FIG. 17, the main body opening portion 61 is located above the fragrance retention container 5 and is opposed, at the main body bottom 64, to the container opening portion 60 formed at the top face 23 of the fragrance retention container 5.

As illustrated in FIG. 15, the inlet side space 24a and the outlet side space 24b are formed as dividing the space in the case 10a into two spaces by the partition plate 17 in the case 10a being arranged in the vertical direction so as to surround the air outlet opening portion 4. The partition plate opening portion 18a formed at the partition plate 17 is a hole at the vicinity of the air outlet opening portion 4a. The partition plate opening portion 18b formed at the partition plate 17 is a hole at the vicinity of the air outlet opening portion 4b. The partition plate opening portion 18a is sized to be capable of being sealed by the outlet passage opening/closing door 9a and the partition plate opening portion 18b is sized to be capable of being sealed by the outlet passage opening/closing door 9b. When the opening portion 56 at one end side communicating with the air inlet opening portion 3a and the opening portion 56 at one end side communicating with the air outlet opening portion 4a are closed, the partition plate opening portion 18a can pass air flow therethrough from the inlet side space 24a to the outlet side space 24b. When the opening portion 56 at one end side communicating with the air inlet opening portion 3b and the opening portion 56 at one end side communicating with the air outlet opening portion 4b are closed, the partition plate opening portion 18b can pass air flow therethrough from the inlet side space 24a to the outlet side space 24b.

Further, as illustrated in FIGS. 15 and 17, the main body 10 includes the inlet passage opening/closing door 8b to open/seal the opening portion 56 at one end side communicating with the air inlet opening portion 3b, the outlet passage opening/closing door 9b to open/seal the opening portion 56 at one end side communicating with the air outlet opening portion 4b, the inlet passage opening/closing door 8a to open/seal the opening portion 56 at one end side communicating with the air inlet opening portion 3a, and the outlet passage opening/closing door 9a to open/seal the opening portion 56 at one end side communicating with the air outlet opening portion 4a. As illustrated in FIG. 14, the case 10a further includes the rotary shaft 12a to open/close the inlet passage opening/closing door 8a and the outlet passage opening/closing door 9a and the rotary shaft 12b to open/close the inlet passage opening/closing door 8b and the outlet passage opening/closing door 9b.

As illustrated in FIG. 15, the outlet passage opening/closing door 9a seals the partition plate opening portion 18a while the opening portion 56 at one end side communicating with the air outlet opening portion 4a is kept opened and opens the partition plate opening portion 18a while the opening portion 56 at one end side communicating with the air outlet opening portion 4a is kept sealed. The outlet passage opening/closing door 9b seals the partition plate opening portion 18b while the opening portion 56 at one end side communicating with the air outlet opening portion 4b is kept opened and opens the partition plate opening portion 18b while the opening portion 56 at one end side communicating with the air outlet opening portion 4b is kept sealed.

The inlet passage opening/closing door 8a may be formed as any opening/closing type in any shape as long as the opening portion 56 at one end side communicating with the air inlet opening portion 3a can be opened and sealed as illustrated in FIG. 17. The inlet passage opening/closing door 8b may be formed as any opening/closing type in any shape as long as the opening portion 56 at one end side communicating with the air inlet opening portion 3b can be opened and sealed. The outlet passage opening/closing door 9a may be formed as any opening/closing type in any shape as long as the opening portion 56 at one end side communicating with the air outlet opening portion 4a can be opened and sealed and the partition plate opening portion 18a can be opened and sealed. The outlet passage opening/closing door 9b may be formed as any opening/closing type in any shape as long as the opening portion 56 at one end side communicating with the air outlet opening portion 4b can be opened and sealed and the partition plate opening portion 18b can be opened and sealed. Here, the rotary shaft 12a and the rotary shaft 12b are rotated in a state of penetrating through the partition plate 17 and the case 10a.

Next, the sealing component 50 according to the first embodiment is formed of elastic material and is sandwiched at the mating faces of the fragrance retention container 5 and the main body 10, as illustrated in FIG. 17. Further, the sealing component 50 includes the hole portion 53, the door side pressure-contact portion 54 and the container side pressure-contact portion 55. The door side pressure-contact portion 54 and the container side pressure-contact portion 55 are integrally formed so that air flow can pass between the opening portion 56 at one end side of the hole portion 53 at the door side pressure-contact portion 54 side and the opening portion 57 at the other end side of the hole portion 53 at the container side pressure-contact portion 55 side. With the above configuration, it is possible to provide the sealing component 50 having less sealing positions and less part count. Specifically, when the door side pressure-contact portion 54 and the container side pressure-contact portion 55 is separated, there are four sealing positions as being i) a sealing position between the passage opening/closing door 62 and the door side pressure-contact portion 54, ii) a sealing position between the door side pressure-contact portion 54 and the inside of the main body bottom 64, iii) a sealing position between the container side pressure-contact portion 55 and the outside of the main body bottom 64, and iv) a sealing position between the container side pressure-contact portion 55 and the container top face 23 of the fragrance retention container 5. However, when the door side pressure-contact portion 54 and the container side pressure-contact portion 55 are integrated, there are two sealing positions as being i) the sealing position between the passage opening/closing door 62 and the door side pressure-contact portion 54 and iv) the sealing position between the container side pressure-contact portion 55 and the container top face 23 of the fragrance retention container 5.

As illustrated in FIG. 17, the hole portion 53 is the hole causing communication between the accommodation space 2 at which the container opening portion 60 is sealed by the sealing component 50 and the main body internal space 24. In order to ensure sealing ability as pressure-contacting the opening portion 56 at one end side to the passage opening/closing door 62, it is preferable that the hole portion 53 is a single through hole. Further, it is preferable that length of the hole portion 53 is longer than a distance between the closed position of the passage opening/closing door 62 and the container opening portion 60.

As illustrated in FIG. 17, the door side pressure-contact portion 54 is disposed at one end side of the sealing component 50. The one end side is placed in main body internal space 24. Then, when the passage opening/closing door 62 is closed, the opening portion 56 at the one end side of the hole portion 53 is closed as being pressure-contacted by the door face of the passage opening/closing door 62. Further, it is preferable that a center portion 58 of a section of the door side pressure-contact portion 54 placed in the main body internal space 24 has a larger outer diameter than the diameter of the main body opening portion 61. With the above configuration, the door side pressure-contact portion 54 having the center portion 58 of which outer diameter is larger than the diameter of the main body opening portion 61 is fitted to the main body opening portion 61 of which diameter is smaller than that of the center portion 58 of the door side pressure-contact portion 54. Accordingly, the sealing component 50 can be assembled easily and reliably. That is, when the outer diameter of the opening portion 56 at the one end side is set to be smaller than the diameter of the main body opening portion 61, the opening portion 56 at the one end side can be easily inserted to the main body opening portion 61 for fitting. Then, since the outer diameter of the center portion 58 of the door side pressure-contact portion 54 is larger than the diameter of the main body opening portion 61, the sealing component 50 does not drop accidentally after the door side pressure-contact portion 54 is once fitted. Further, when the opening portion 56 at the one end side of the hole portion 53 is pressure-contacted by the passage opening/closing door 62, the opening portion 56 at the one end side of the door side pressure-contact portion 54 follows without straining as the center portion 58 of the door side pressure-contact portion 54 being a strain position to be compressed. Accordingly, sealing ability between the passage opening/closing door 62 and the sealing component 50 can be improved.

The container side pressure-contact portion 55 is arranged at the other end side of the sealing component 50. As illustrated in FIG. 17, the other end side is placed between the fragrance retention container 5 and the main body 10. With the above configuration, the opening portion 57 at the other end side seals the container opening portion 60 as the container side pressure-contact portion 55 being sandwiched and pressure-contacted by the fragrance retention container 5 and the main body 10. Being different from the door side pressure-contact portion 54, the container side pressure-contact portion 55 is continuously pressure-contacted when the fragrance retention container 5 is kept attached to the main body 10. With the above configuration, the accommodation space 2 and the hole portion 53 of the sealing component 50 are sealed at the pressure-contact position. Here, it is preferable that a center portion 71 of a section of the container side pressure-contact portion 55 placed in the main body internal space 24 has a larger outer diameter than the diameter of the main body opening portion 61. When the opening portion 57 at the other end side of the hole portion 53 is pressure-contacted to the container opening portion 60, the opening portion 57 at the other end side follows without straining as the center portion 71 of the container side pressure-contact portion 55 being a strain position to be compressed. Accordingly, sealing ability between the sealing component 50 and the container opening portion 60 of the fragrance retention container 5 can be improved. Here, the inner diameter of the opening portion 57 at the other end side is set to be the same as the diameter of the container opening portion 60 (3a, 3b, 4a, 4b). However, for performing sealing, it is also possible to set the inner diameter of the opening portion 57 at the other end side to be larger than the diameter of the container opening portion 60 (not illustrated). Further, the opening portion 57 at the other end side may be placed in the accommodation space 2. In this case, it is also possible to set the inner diameter of the opening portion 57 at the other end side to be smaller than the diameter of the container opening portion 60 (not illustrated). Here, in this case, it is required to arrange a pressure-contact portion (not illustrated) for ensuring sealing between the container opening portion 60 and a side wall of the sealing component 50 at the other end side.

Figure 20:
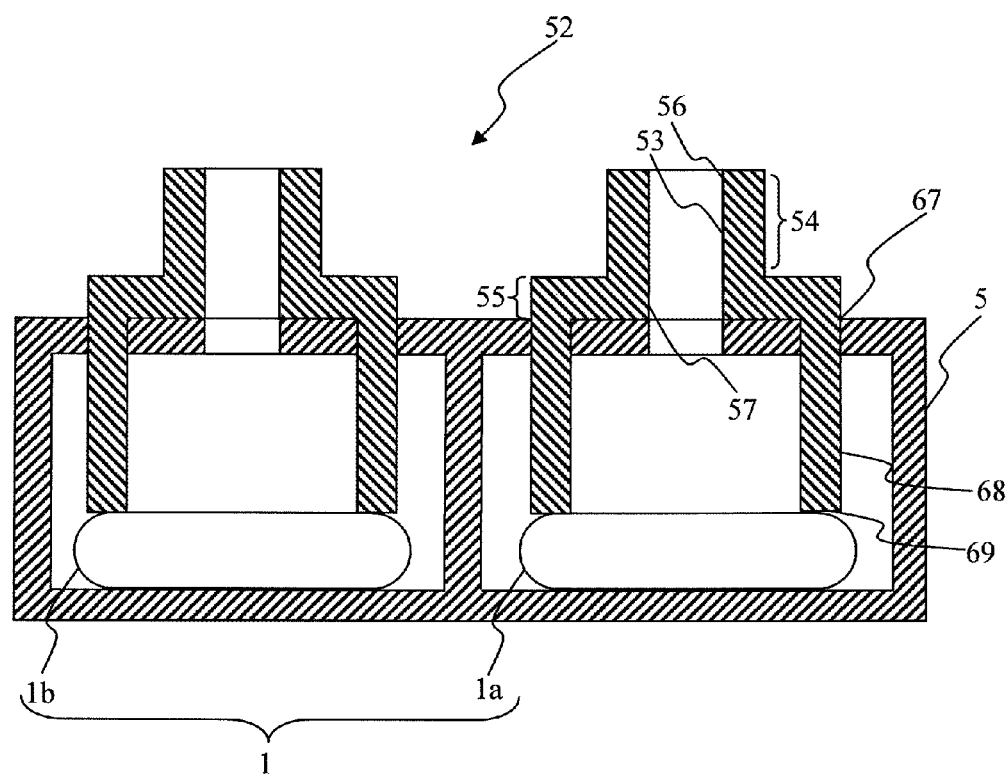
FIG. 20 is a vertically-sectioned schematic view of a sealing component according to the third embodiment attached to the fragrance retention container.

Further, a sealing component 52 according to the third embodiment in FIG. 20 is illustrated as another example. The sealing component 52 includes a fragrance support portion 68 as the distal end of the container side pressure-contact portion 55 being extended. The sealing component 52 is attached to the fragrance retention container 5 by inserting the fragrance support portion 68 to the support portion insertion hole 67. Then, a distal end portion 69 of the fragrance support portion 68 fixes the fragrant agent 1 as pressing. It is preferable that two or more of the fragrance support portions 68 are arranged so as to stably hold the fragrant agent 1. With the above configuration, when the fragrance retention container 5 is assembled to the main body 10, sealing ability due to the sealing component 52 is inevitably ensured. Accordingly, operability of assembling and robustness can be improved. In addition, the fragrant agent 1 can be reliably fixed by the fragrance support portion 68 as the container side pressure-contact portion 55 being extended. Accordingly, it is possible to prevent breakage of the fragrant agent 1 due to vibration and noise generated by movement of the fragrant agent 1.

Further, it is preferable that the container side pressure-contact portion 55 seals the main body opening portion 61 as illustrated in FIG. 17. With the above configuration, the container side pressure-contact portion 55 blocks a gap between the main body opening portion 61 and the side wall of the sealing component 50, so that leakage of air flow from the main body internal space 24 to a space 70 between the main body 10 and the fragrance retention container 5 can be reliably prevented without relation to opening/closing of the passage opening/closing door 62. Here, there is a case that some gap is generated between an inner edge 61a of the main body opening portion 61 and the side wall of the sealing component 50. In order to prevent leakage from such a gap, it is preferable that the container side pressure-contact portion 55 is provided with a plate-shaped portion 59. Further, it is also possible to make the side wall of the sealing component 50 pressure-contacted to the inner edge 61a of the main body opening portion 61 as the outer diameter of the sealing component 50 being set to be larger than the diameter of the main body opening portion 61.

Figure 16:
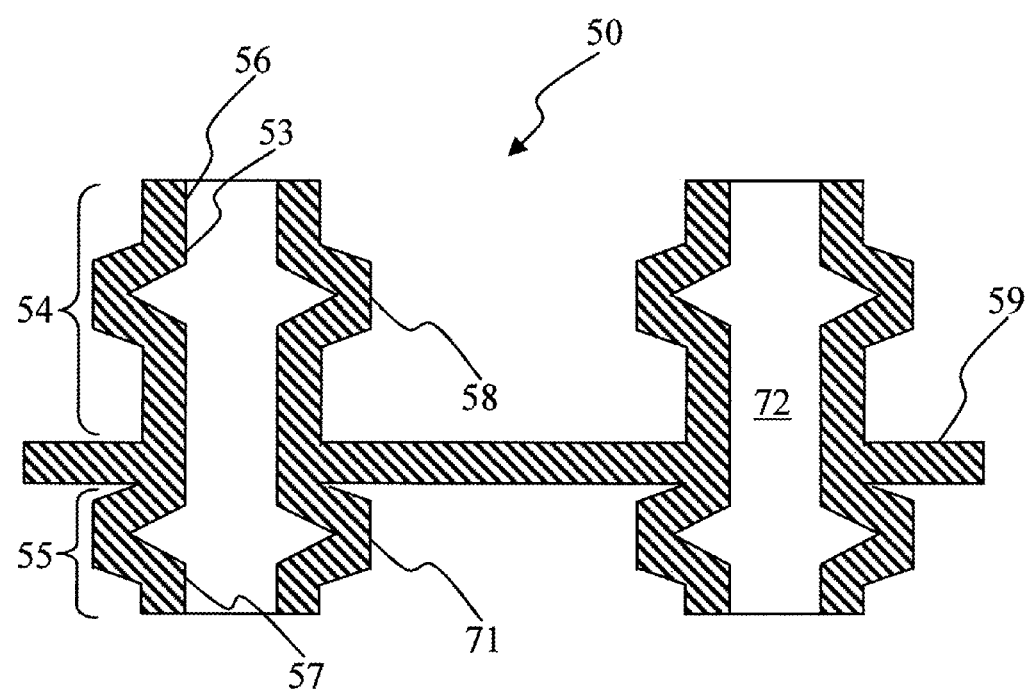
FIG. 16 is a vertically-sectioned schematic view of the sealing component according to the first embodiment.

Further, as illustrated in FIGS. 16 and 17, it is preferable to have plural through pathways 72 respectively constituted with the hole portion 53, the door side pressure-contact portion 54 and the container side pressure-contact portion 55, that is, the plural through pathways 72 due to hole portions 53 and to integrally form the whole. In FIG. 17, two pathways are illustrated. As the number of the pathways in sum of inlet and outlet, two pathways are required for one kind of fragrant agent. For example, four pathways are required for two kinds of fragrant agents. It is similar to a case of having more kinds of fragrant agents 1. Here, as an example that the whole is integrally formed, FIGS. 16 and 17 illustrate an example that the through pathways 72 respectively constituted with the hole portion 53, the door side pressure-contact portion 54 and the container side pressure-contact portion 55 are integrated in a parallel state via the plate-shaped portion 59, as illustrated in FIG. 14 as a perspective view. With the above configuration, the sealing component 50 having plural through pathways 72 can be formed as one part count even when the fragrance retention container 5 includes a plurality of the accommodation spaces 2 or a plurality of the air inlet opening portions 3 and the air outlet opening portions 4. Accordingly, operability can be improved for assembling or replacing the sealing component 50.

The elastic material used for the sealing component 50 is an elastomer, butyl rubber or silicone series rubber, for example. Elastomers are basically classified into thermosetting elastomers (TSE) and thermoplastic elastomers (TPE). In the present embodiment, it is preferable to adopt a thermoplastic elastomer. Thermoplastic elastomers have characteristics to show fluidity as being softened when heated and to return to be elastic when cooled. Accordingly, molding and processing can be rapidly performed with injection molding. Further, thermoplastic elastomers are subdivided into styrene series, olefin series, polyvinyl chloride series, urethane polyester nylon series and amide series. In the present embodiment, it is preferable to use an elastomer of olefin series which is easily processable. Specifically, it is also possible to use a dynamically-cross-linked olefin series elastomer capable of coating an olefin series elastomer. It is possible to obtain the sealing component having superior durability and barrier properties against fragrant ingredients by using an elastomer.

Butyl rubber being a polymer of isobutene and isoprene (i.e., isobutene isoprene rubber: IIR) has low permeability to gases. Alternatively, not limited to butyl rubber, it is also possible to use halogenated butyl rubber. Halogenated butyl rubber includes chlorine butyl rubber (i.e., chlorine IIR: CIIR) and bromine butyl rubber (i.e., bromine IIR: BIIR). Both of the above are improved in cross-linking performance, thermostability and adhesiveness while maintaining characteristics of butyl rubber. It is possible to obtain the sealing component having superior barrier properties against fragrant ingredients by using butyl rubber.

Silicone series rubber being artificial polymer compounds skeletally formed of silicon and oxygen has high thermostablity. Silicone rubber is classified into hot curing silicone rubber and room temperature curing silicone rubber in accordance with curing types. In the present embodiment, it is preferable to use hot curing silicone rubber which is suitable for face-bonding. Examples of silicone series rubber include vinyl methyl silicone rubber or fluorinated silicone rubber which is superior in oil resistance and solvent resistance. It is possible to obtain the sealing component having superior durability by using silicone series rubber.

Figure 18:
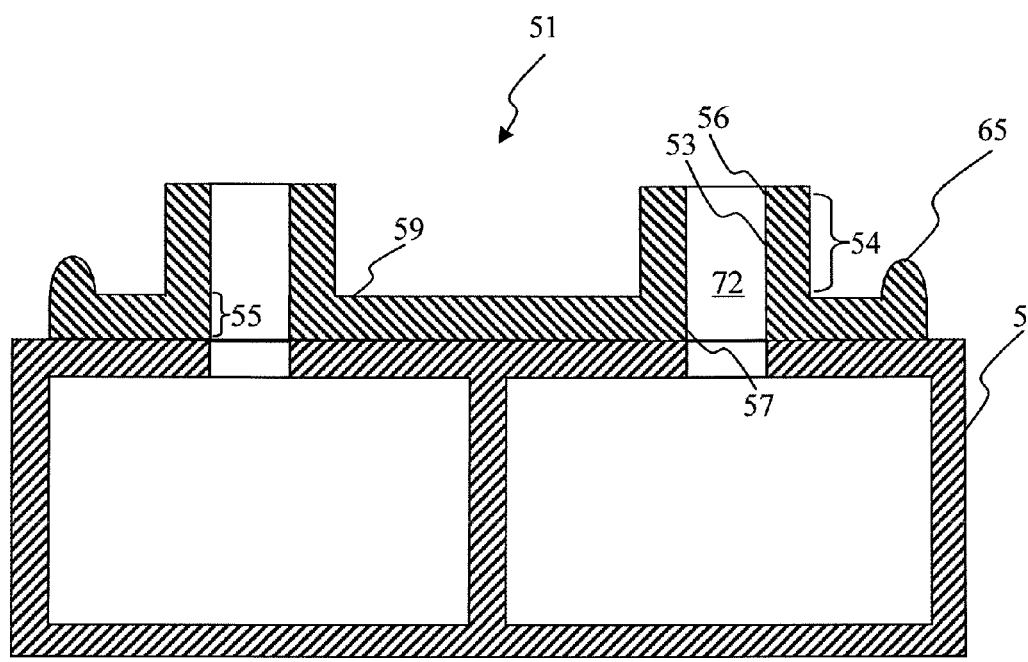
FIG. 18 is a vertically-sectioned schematic view of the sealing component according to the second embodiment which is thermally deposited to the fragrance retention container.
Figure 19A:
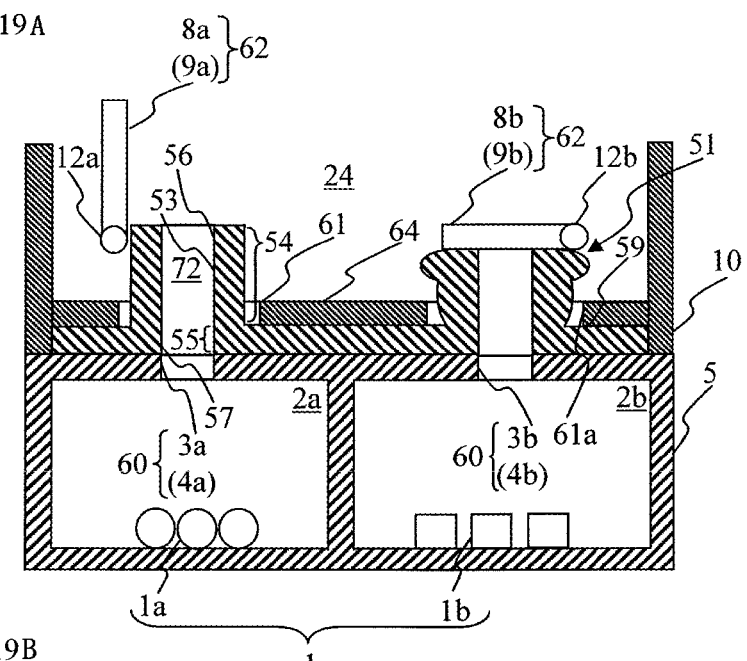
FIG. 19A illustrates a state that one door is opened and the other door is closed.
Figure 19B:
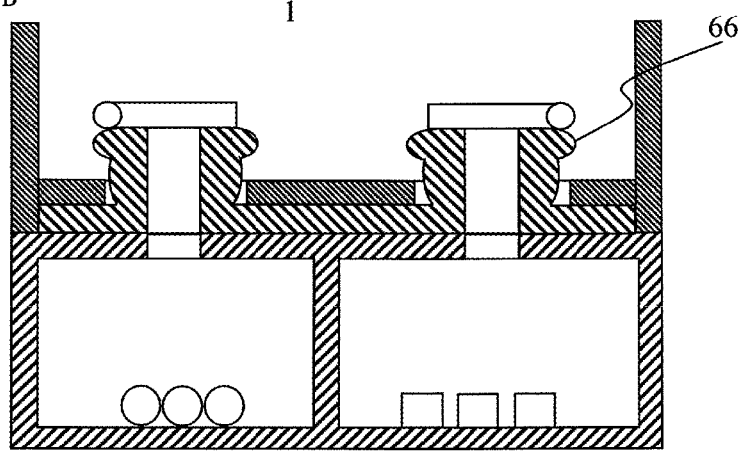
FIG. 19B illustrates a state that all doors are closed.
Figure 19C:
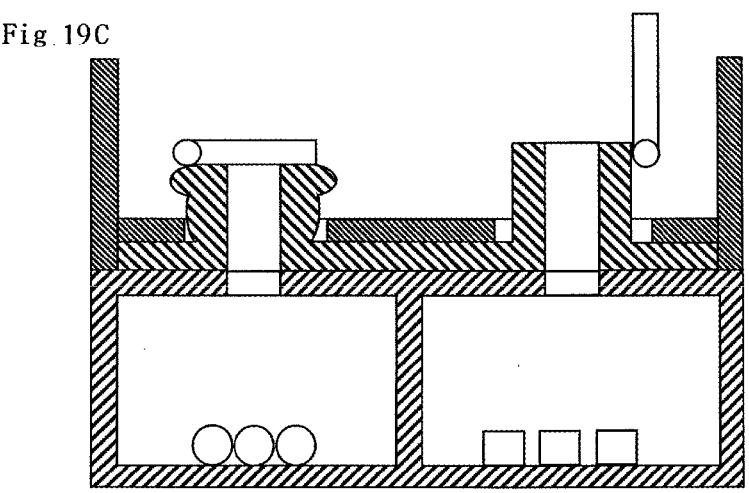
FIG. 19C illustrates a state that the one door is closed and the other door is opened.

Since thermal deposition can be performed when a thermoplastic elastomer is used as the elastic material for the sealing component, it is preferable that the sealing component 51 is integrated with the fragrance retention container 5 as illustrated in FIG. 18. Such an integrated structure can be obtained by placing the molded fragrance retention container 5 in a mold and by molding as thermally depositing an elastomer in the mold. Since the sealing component 51 having the container side pressure-contact portion 55 thermally-deposited thereto is integrated with the fragrance retention container 5, it is not required to seal the position between the container side pressure-contact portion 55 and the container top face 23 of the fragrance retention container 5. Accordingly, the sealing position remains only between the door side pressure-contact portion 54 and the passage opening/closing door 62. In this manner, reliable sealing can be obtained while reducing part count. Further, since the sealing component 51 can be assembled or replaced along with the fragrance retention container 5, it is possible to eliminate a risk of missing of the sealing component 51. Then, when the fragrance retention container 5 is assembled to the main body 10, sealing ability due to the sealing component 51 is inevitably ensured. Accordingly, operability of assembling and robustness can be improved. It is also possible that the sealing component 51 includes a protruding portion 65 so as to surround the container opening portion 60. The protruding portion 65 ensures higher sealing ability as eliminating the gap by being deformed as being compressed between the fragrance retention container 5 and the main body bottom 64 when the fragrance retention container 5 is assembled to the main body 10. Further, the protruding portion 65 may be formed at the position to isolate each through pathways 72 for the plural through pathways 72. Then, as illustrated in FIG. 19A or FIG. 19B, the opening portion 56 of the door side pressure-contact portion 54 at one end side is deformed as being pressure-contacted by the passage opening/closing door 62 and causes the pressure-contacted opening portion 66. The pressure-contacted opening portion 66 ensures sealing ability between the opening portion 56 at the one end side and the passage opening/closing door 62.

Any of the sealing components according to the present invention is arranged to the fragrance device 100 for a vehicle. The fragrance device 100 for a vehicle which intermittently supplies fragrant ingredients owing to door opening/closing is easily manufactured and reliably assembled, and then, can supply a desired fragrant ingredient when desired and can prevent unintentional volatilization of fragrant ingredients when not desired owing to superior sealing ability.

Figure 21:
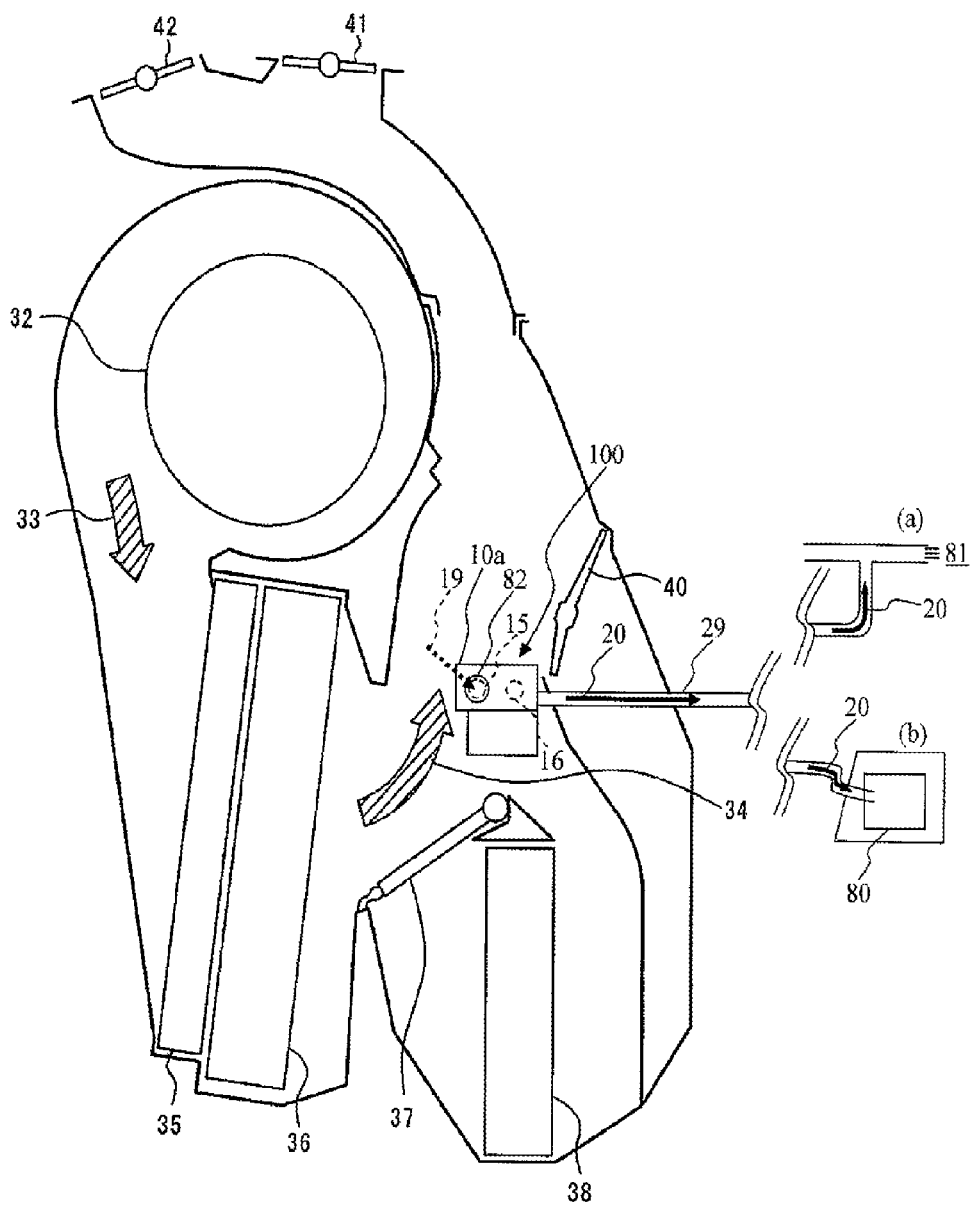
FIG. 21 is a schematic sectional view of the connection relation with a vehicle-use air-conditioning device as illustrating another embodiment of arrangement of the fragrance device for a vehicle.

Next, another aspect of an arrangement example of the fragrance device 100 for a vehicle using the sealing component according to the present embodiment will be described with reference to a schematic sectional view of FIG. 21. As illustrated in FIG. 21, a hole 82 opens at an outer wall of a case of a vehicle-use air-conditioning device. The inlet 15 is inserted to the hole 82 so as to inpour the air flow 19. Thus, the case 10*a* of the fragrance device 100 for a vehicle covers the hole 82 of the outer wall of the vehicle-use air-conditioning device. Further, the outlet 16 directly supply the air flow 20 containing a fragrant ingredient to the vehicle inside 81 as illustrated in FIG. 21A or to a section before an outlet port 80 as illustrated in FIG. 21B via the outlet pipe 29. With the above configuration, the inlet pipe 28 illustrated in FIG. 5 becomes unnecessary in the aspect illustrated in FIG. 21, so that part count can be reduced. Further, temperature-adjusted air flow 19 can be inpoured to the inlet 15 from an air-mix chamber or a side vent. Here, in FIG. 21, the hole 82 is formed at the air-mix chamber at the downstream of the filter 35 and the evaporator 36. It is also possible to adopt the similar arrangement to that illustrated in FIG. 21 in the configuration of FIG. 5. Next, flow of the air flow will be described. First, the blower 32 installed in the vehicle-use air-conditioning device outpours the air flow 33. Pressure of the air flow 33 is increased as being compressed toward the filter 35 and the evaporator 36 installed in the vehicle-use air-conditioning device. The air flow 19 being a part of the air flow 34 at the downstream of the filter 35 and the evaporator 36 is inpoured to the inlet passage 6 of the fragrance device 100 for a vehicle via the inlet 15. In the fragrance device 100 for a vehicle, all or a part of the air flow 19 contains a fragrant ingredient to be the air flow 20 containing the fragrant ingredient. The air flow 20 containing the fragrant ingredient is supplied to the vehicle inside 81 as illustrated in FIG. 21A or the section before the outlet port 80 as illustrated in FIG. 21B having lowered pressure from the outlet passage 7 via the outlet 16. Here, the inlet 15 may be placed at any position as long as pressure difference is generated.

Next, operation of the sealing component according to the present embodiment and the fragrance device 100 for a vehicle incorporating the sealing component will be described with reference to FIGS. 5, 6, 17, 18 and 20. As illustrated in FIGS. 6A and 17A, the inlet passage opening/closing door 8*a* opens the air inlet opening portion 3*a* as departing from the opening portion 56 of the hole portion 53 at one end side. The outlet passage opening/closing door 9*a* opens the air outlet opening portion 4*a* as departing from the opening portion 56 of the hole portion 53 at one end side and closes the partition plate opening portion 18*a*. The inlet passage opening/closing door 8*b* closes the air inlet opening portion 3*b* by closing the opening portion 56 of the hole portion 53 at one end side with pressure-contact. The outlet passage opening/closing door 9*b* closes the air outlet opening portion 4*b* by closing the opening portion 56 of the hole portion 53 at one end side with pressure-contact and opens the partition plate opening portion 18*b*. A part of the air flow 19 inpoured to the inlet passage 6 from the inlet 15 flows to the opening portion 57 at the other end side from the opening portion 56 at the one end side via the through pathway 72, and then, flows into the accommodation space 2*a* from the air inlet opening portion 3*a* communicating with the opening portion 57 at the other end side to be the air flow 29*a* containing a fragrant ingredient as containing the fragrant ingredient of the fragrant agent 1*a*. The air flow 29*a* containing the fragrant ingredient passes through the air outlet opening portion 4*a* communicating with the opening portion 57 at the other end side from the inside of the accommodation space 2*a* and flows to the outlet passage 7 as flowing to the opening portion 56 at the one end side via the through pathway 72 from the opening portion 57 at the other end side. Meanwhile, other air flow 30*a* which is not inpoured into the accommodation space 2*b* from the air inlet opening portion 3*b* flows to the outlet passage 7 through the partition plate opening portion 18*a* from the inlet passage 6. The air flow 20*a* being mixture of the air flow 30*a* with the air flow 29*a* containing the fragrant ingredient is supplied to the vehicle inside as being outpoured from the end part 31*b* of the outlet pipe 29 via the outlet 16, as illustrated in FIG. 5. Then, after predetermined time passes, the state shifts to that illustrated in FIG. 6B. By the way, similar operation is performed even in a case of utilizing the sealing component 51 according to the second embodiment as being thermally deposited to the fragrance retention container 5 as illustrated in FIG. 18 or the sealing component 52 according to the third embodiment as being mounted on the fragrance retention container 5 as illustrated in FIG. 20.

As illustrated in FIGS. 6B and 17B, the outlet passage opening/closing door 9*a* closes the opening portion 56 of the hole portion 53 at the one end side with pressure-contact and opens the partition plate opening portion 18*a*. The outlet passage opening/closing door 9*b* closes the opening portion 56 of the hole portion 53 at the one end side with pressure-contact and opens the partition plate opening portion 18*b*. The air flow 19 inpoured to the inlet passage 6 from the inlet 15 is outpoured from the end part 31*b* of the outlet pipe 29, as illustrated in FIG. 5, via the outlet passage 7 and the outlet 16 after passing through the partition plate opening portion 18*a* and the partition plate opening portion 18*b*. Accordingly, only air flow 20*b* which does not contain any fragrant ingredient is supplied to the vehicle inside. By the way, similar operation is performed even in a case of utilizing the sealing component 51 according to the second embodiment as being thermally deposited to the fragrance retention container 5 as illustrated in FIG. 18 or the sealing component 52 according to the third embodiment as being mounted on the fragrance retention container 5 as illustrated in FIG. 20.

Here, the main body 10 includes the inlet passage opening/closing door 8 for each air inlet opening portion 3 and the outlet passage opening/closing door 9 for each air outlet opening portion 4 and is configured so that the inlet passage 6 and the outlet passage 7 become a directly connected passage when the opening portions 56 at the one end side communicating with all of the air inlet opening portion 3 and the air outlet opening portion 4 are closed with pressure-contact. By forming the inlet passage 6 and the outlet passage 7 to be the directly-connected passage when the opening portions 56 at the one end side communicating with all of the air inlet opening portion 3 and the air outlet opening portion 4 are closed with pressure-contact, the fragrant ingredient supplied when opening the opening portion 56 at the one end side communicating with any of the air inlet opening portion 3 and the air outlet opening portion 4 as departing therefrom can be ejected owing to the air low 20b which does not contain any fragrant ingredient. In this manner, supplying of the fragrant ingredient is stopped by sealing the opening portions 56 at the one end side communicating with the air inlet opening portion 3 and the air outlet opening portion 4 with pressure contact, so that the fragrant ingredient can be prevented from being wasted.

The cam 14 causes a mode in which all of the inlet passage opening/closing door 8 and the outlet passage opening/closing door 9 are closed to occur on the way when the inlet passage opening/closing door 8 and the outlet passage opening/closing door 9 corresponding to the opening portions 56 at the one end side communicating with the air inlet opening portion 3 and the air outlet opening portion 4 of one accommodation space 2 are being switched from an opened state to a closed state and the inlet passage opening/closing door 8 and the outlet passage opening/closing door 9 corresponding to the opening portions 56 at the one end side communicating with the air inlet opening portion 3 and the air outlet opening portion 4 of the other accommodation space 2 are being switched from a closed state to an opened state. By switching plural fragrant ingredients through the mode in which all of the inlet passage opening/closing door 8 and the outlet passage opening/closing door 9 are closed, the air flow 20b which does not contain any fragrant ingredient ejects the fragrant ingredient remaining in the outlet passage 7 and the outlet pipe 29. Accordingly, the plural fragrant ingredients are not mixed.

Subsequently, the state of FIGS. 6B and 17B is shifted to the state illustrated in FIGS. 6C and 17C after predetermined time passes. As illustrated in FIGS. 6C and 17C, the inlet passage opening/closing door 8b opens the air inlet opening portion 3b as departing from the opening portion 56 of the hole portion 53 at the one end side. The outlet passage opening/closing door 9b opens the air outlet opening portion 4b as departing from the opening portion 56 of the hole portion 53 at the one end side and closes the partition plate opening portion 18b. The inlet passage opening/closing door 8a closes the air inlet opening portion 3a by closing the opening portion 56 of the hole portion 53 at the one end side with pressure contact. The outlet passage opening/closing door 9a closes the air outlet opening portion 4a by closing the opening portion 56 of the hole portion 53 at the one end side with pressure contact and opens the partition plate opening portion 18a. A part of the air flow 19 inpoured to the inlet passage 6 from the inlet 15 flows to the opening portion 57 at the other end side from the opening portion 56 at the one end side via the through pathway 72, and then, flows into the accommodation space 2b from the air inlet opening portion 3b communicating with the opening portion 57 at the other end side to be the air flow 29c containing a fragrant ingredient as containing the fragrant ingredient of the fragrant agent 1b. The air flow 29c containing the fragrant ingredient passes through the air outlet opening portion 4b communicating with the opening portion 57 at the other end side from the inside of the accommodation space 2b and flows to the outlet passage 7 as flowing to the opening portion 56 at the one end side via the through pathway 72 from the opening portion 57 at the other end side. Meanwhile, other air flow 30c which is not inpoured into the accommodation space 2b from the air inlet opening portion 3b flows to the outlet passage 7 through the partition plate opening portion 18b from the inlet passage 6. The air flow 20c being mixture of the air flow 30c with the air flow 29c containing the fragrant ingredient is supplied to the vehicle inside as being outpoured from the end part 31b of the outlet pipe 29 via the outlet 16, as illustrated in FIG. 5. Then, after predetermined time passes, the state shifts to that illustrated in FIG. 6B. By the way, similar operation is performed even in a case of utilizing the sealing component 51 according to the second embodiment as being thermally deposited to the fragrance retention container 5 as illustrated in FIG. 18 or the sealing component 52 according to the third embodiment as being mounted on the fragrance retention container 5 as illustrated in FIG. 20.

Subsequently, with repeated to-and-fro operation in the order of FIG. 6A→FIG 6B→FIG. 6C→FIG. 6B→FIG. 6A . . ., supplying to the vehicle inside is repeatedly performed in the order of the air flow 20a, the air flow 20b, the air flow 20c, the air flow 20b, the air flow 20a . . . . Alternatively, as needed basis, the air flow 20a and the air flow 20b are alternately supplied to the vehicle inside with repeated operation of FIG. 6A and FIG. 6B or the air flow 20b and the air flow 20c are alternately supplied to the vehicle inside with repeated operation of FIG. 6B and FIG. 6C. Here, the air flow 20 containing a fragrant ingredient illustrated in FIG. 5 includes the air flow 20a, the air flow 20b and the air flow 20c.

Here, when the blower 32 of the vehicle-use air-conditioning device is stopped or the ignition of the vehicle is turned off in a state that a fragrant ingredient is supplied as the opening portions 56 at one end side communicating with the air inlet opening portion 3 and the air outlet opening portion 4 being opened, it is preferable that a control unit (not illustrated) performs control to close the opening portions 56 at the one end side communicating with the air inlet opening portion 3 and the air outlet opening portion 4. Fragrant agents can be prevented from being wasted by closing the opening portions 56 at the one end side communicating with the air inlet opening portion 3 and the air outlet opening portion 4 when a fragrant ingredient is not required to be supplied.

Further, it is also possible to arrange a door (not illustrated) which closes the partition plate opening portion 18 in synchronization with closing of the opening portion 56 at one end side communicating with the air outlet opening portion 4 by the outlet passage opening/closing door 9 during non-supplying of a fragrant ingredient. Alternatively, it is also possible to arrange a door which closes the opening portion 15d formed at the connection portion 15c between the case 10a and the inlet pipe 15b and a door (not illustrated) which closes the opening portion 16d formed at the connection portion 16c between the case 10a and the outlet pipe 16b in synchronization with closing of the opening portion 56 at one end side communicating with the air outlet opening portion 4 by the outlet passage opening/closing door 9 during non-supplying of a fragrant ingredient. With the above configuration, temperature adjustment can be performed for all air flow 33 as eliminating air flow 19 passing through the main body internal space 24 during non-supplying of a fragrant ingredient, so that temperature adjustment due to the vehicle-use air-conditioning device can be reliably performed.

Explanations of Reference Numerals

100 Fragrance device for a vehicle of the first embodiment
101 Fragrance device for a vehicle of the second embodiment
102 Fragrance device for a vehicle of the third embodiment
1 Fragrant agent
1a Fragrant agent a
1b Fragrant agent b 2 Accommodation space
2a Accommodation space a
2b Accommodation space b
3 Air inlet opening portion
3a Air inlet opening portion a
3b Air inlet opening portion b
4 Air outlet opening portion
4a Air outlet opening portion a
4b Air outlet opening portion b
5 Fragrance retention container
6 Inlet passage
7 Outlet passage
8 Inlet passage opening/closing door
8a Inlet passage opening/closing door a
8b Inlet passage opening/closing door b
9 Outlet passage opening/closing door
9a Outlet passage opening/closing door a
9b Outlet passage opening/closing door b
10 Main body
10a Case
10b Cover
11 Actuator
12 Rotary shaft
12a Rotary shaft a
12b Rotary shaft b
13 Rotary shaft
13a Rotary shaft a (Inlet door shaft for accommodation space 2a)
13b Rotary shaft b (Inlet door shaft for accommodation space 2b)
13c Rotary shaft c (Outlet door shaft for accommodation space 2a)
13d Rotary shaft d (Outlet door shaft for accommodation space 2b)
14 Cam
15 Inlet
15a Inlet opening portion
15b Inlet pipe
15c Connection portion between case 10a and inlet pipe 15b
15d Opening portion at connection portion 15c between case 10a and inlet pipe 15b
16 Outlet
16a Outlet opening portion
16b Outlet pipe
16c Connection portion between case 10a and outlet pipe 16b
16d Opening portion at connection portion 16c between case 10a and outlet pipe 16b
17 Partition plate
18 Partition plate opening portion
18a Partition plate opening portion a
18b Partition plate opening portion b
19 Air flow
20 Air flow containing fragrant ingredient
20a Air flow of mixture of air flow 30a and air flow 29a containing fragrant ingredient
20b Air flow without containing fragrant ingredient
20c Air flow of mixture of air flow 30c and air flow 29c containing fragrant ingredient
21 Trajectory groove
22 Intra-container partition plate
23 Container top face
24 Main body internal space
24a Inlet side space
24b Outlet side space
25 Arm
25a Arm a
25b Arm b
26 Pin
26a Pin a
26b Pin b
27 Actuator shaft
28 Inlet pipe
29 Outlet pipe
29a Air flow containing fragrant ingredient as containing fragrant ingredient of fragrant agent 1a
29c Air flow containing fragrant ingredient as containing fragrant ingredient of fragrant agent 1b
30a Other air flow without being inpoured into accommodation space 2a from air inlet opening portion 3a
30c Other air flow without being inpoured into accommodation space 2b from air inlet opening portion 3b
31 End part of pipe
31a End part of inlet pipe
31b End part of outlet pipe
32 Blower
33 Air flow
34 Blowing air flow
35 Filter
36 Evaporator
37 Air-mixing door
38 Heater core
39 Shortcut hole
39a Inlet of shortcut hole
39b Outlet of shortcut hole
40 Foot door
41 Vent door
42 Defrost door
43 Bag
44 Dummy member
50, 51, 52 Sealing component
53 Hole portion
54 Door side pressure-contact portion
55 Container side pressure-contact portion
56 Opening portion at one end side
57 Opening portion at other end side
58 Center portion of door side pressure-contact portion
59 Plate-shaped portion
60 Container opening portion
61 Main body opening portion
61a Inner edge of main body opening portion
62 Passage opening/closing door
63 Air flow passage
64 Main body bottom
65 Protruding portion
66 Pressure-contacted opening portion
67 Support portion insertion hole
68 Fragrance support portion
69 Distal end portion
70 Space between main body internal bottom face and top face of fragrance retention container
71 Center portion of container side pressure-contact portion
72 Through pathway
80 Outlet port
81 Vehicle inside
82 Hole

The invention claimed is:

1. A fragrance device for a vehicle capable of supplying a fragrant ingredient of a fragrant agent to the inside of the vehicle as being contained in air flow, the fragrance device comprising:
a fragrance retention container including an accommodation space to accommodate a fragrant agent, an air inlet opening portion and an air outlet opening portion;

a main body to which the fragrance retention container is attached and which includes an inlet passage to inpour air to the air inlet opening portion, an outlet passage to outpour air containing the fragrant ingredient from the air outlet opening portion, an inlet passage opening/closing door to open/close the air inlet opening portion, and an outlet passage opening/closing door to open/close the air outlet opening portion;

an actuator fixed to the main body;

a cam which is connected to the actuator and which rotationally drives a first rotary shaft portion of the inlet passage opening/closing door and a second rotary shaft portion of the outlet passage opening/closing door.

2. The fragrance device for a vehicle according to claim 1, wherein the inlet passage opening/closing door and the outlet passage opening/closing door are attached to a single rotary shaft at positions where opening/closing of the air inlet opening portion and the air outlet opening portion are synchronized.

3. The fragrance device for a vehicle according to claim 1, wherein the fragrance retention container includes plural accommodation spaces for respectively accommodating plural fragrant agents, and the air inlet opening portion and the air outlet opening portion for each accommodation space;

the main body includes the inlet passage opening/closing door for each air inlet opening portion and the outlet passage opening/closing door for each air outlet opening portion; and the inlet passage and the outlet passage become a directly-connected passage when all of the air inlet opening portions and the air outlet opening portions are closed.

4. The fragrance device for a vehicle according to claim 3, wherein the cam causes a mode in which all of the inlet passage opening/closing doors and the outlet passage opening/closing doors are closed to occur on the way when the inlet passage opening/closing door and the outlet passage opening/closing door corresponding to the air inlet opening portion and the air outlet opening portion of an accommodation space are being switched from an opened state to a closed state and the inlet passage opening/closing door and the outlet passage opening/closing door corresponding to the air inlet opening portion and the air outlet opening portion of another accommodation space are being switched from a closed state to an opened state.

5. The fragrance device for a vehicle according to claim 1, wherein the fragrance retention container includes plural accommodation spaces for respectively accommodating plural fragrant agents, and the air inlet opening portion and the air outlet opening portion for each accommodation space;

the main body includes the inlet passage opening/closing door for each air inlet opening portion and the outlet passage opening/closing door for each air outlet opening portion; and the cam causes a mode in which all of the inlet passage opening/closing doors and the outlet passage opening/closing doors are closed to occur on the way when the inlet passage opening/closing door and the outlet passage opening/closing door corresponding to the air inlet opening portion and the air outlet opening portion of an accommodation space are being switched from an opened state to a closed state and the inlet passage opening/closing door and the outlet passage opening/closing door corresponding to the air inlet opening portion and the air outlet opening portion of another accommodation space are being switched from a closed state to an opened state.

6. The fragrance device for a vehicle according to claim 1, wherein the fragrance retention container includes respective pluralities of the fragrant agents, the air inlet opening portions, the air outlet opening portions, the inlet passage opening/closing doors, and the outlet passage opening/closing doors;

the inlet passage opening/closing doors and the outlet passage opening/closing doors are attached respectively to a separate rotary shaft at positions where opening/closing of the air inlet opening portions and the air outlet opening portions are synchronized;

the main body includes a shortcut hole which connects the inlet passage and the outlet passage; and any one of the inlet passage opening/closing doors closes an inlet of the shortcut hole when the air inlet opening portion is opened, and any one of the outlet passage opening/closing doors closes an outlet of the shortcut hole when the air outlet opening portion is opened.

7. The fragrance device for a vehicle according to claim 1, wherein the fragrance retention container includes a plurality of the accommodation spaces for accommodating fragrant agents; and volumes of the accommodation spaces respectively differ for each fragrant agent.

8. The fragrance device for a vehicle according to claim 7, wherein the inlet passage opening/closing door and the outlet passage opening/closing door open and close the air inlet opening portion and the air outlet opening portion in synchronization with each other;

the air inlet opening portion and the air outlet opening portion disposed at one accommodation space are being opened or closed when the air inlet opening portion and the air outlet opening portion disposed at the other accommodation space are closed; and the air inlet opening portion and the air outlet opening portion disposed at the other accommodation space are being opened or closed when the air inlet opening portion and the air outlet opening portion disposed at the one accommodation space are closed.

9. The fragrance device for a vehicle according to claim 7, wherein the fragrant agent is solid-like or is a ceramic body supporting a fragrant agent.

10. The fragrance device for a vehicle according to claim 7, wherein the fragrant agents are a fragrant agent A being large and heavy and a fragrant agent B being smaller and lighter than the fragrant agent A;

the fragrant agent A is sized to be incapable of being accommodated in a small-volume accommodation space X and sized to be capable of being accommodated in a large-volume accommodation space Y; and the fragrant agent B is sized to be capable of being accommodated in the accommodation space X.

11. The fragrance device for a vehicle according to claim 7, wherein the fragrant agents are a fragrant agent having a large detection threshold value of a fragrant ingredient and a fragrant agent having a smaller detection threshold value than that of the fragrant agent; and the fragrant agent having the large detection threshold value is accommodated in a large accommodation space and the fragrant agent having the small detection threshold value is accommodated in a smaller accommodation space than the large accommodation space.

12. The fragrance device for a vehicle according to claim 7, wherein the fragrant agents are a fragrant agent having a large evaporation rate of a fragrant ingredient and a fragrant agent having a smaller evaporation rate than the fragrant agent having the large evaporation rate;

the fragrant agent having the large evaporation rate is accommodated in a small accommodation space and the fragrant agent having the small evaporation rate is accommodated in a larger accommodation space than the small accommodation space, or the fragrant agent having the large evaporation rate is accommodated in a large accommodation space and the fragrant agent having the small evaporation rate is accommodated in a smaller accommodation space than the large accommodation space.

13. The fragrance device for a vehicle according to claim 7, wherein the accommodation spaces are set to have different volumes owing to a partitioning ratio of the accommodation spaces with an intra-container partition plate or owing to a volume of a dummy member accommodated in the accommodation space.

14. The fragrance device for a vehicle according to claim 7, wherein the fragrance retention container is formed of resin or resin-based material.

15. The fragrance device for a vehicle according to claim 14, wherein the resin is polypropylene; and the fragrance retention container is formed to have thickness of not less than 1.8 mm and not more than 3.2 mm.

16. A sealing component made of elastic material to be used for the fragrance device for a vehicle according to claim 1, wherein the vehicle-use fragrance device adds a fragrant ingredient of the fragrant agent to air flow of an air-conditioning device as comprising a fragrance retention container which includes an accommodation space to accommodate a fragrant agent and a container opening portion, and a main body including a main body internal space to be an air flow passage, a main body opening portion, and a passage opening/closing door to open/close the main body opening portion from the inside, and as the fragrance retention container being attached to the main body in a state that the accommodation space and the main body internal space are communicated via the container opening portion and the main body opening portion;

the sealing component is sandwiched between mating faces of the fragrance retention container and the main body and is provided with a hole portion which causes communication between the accommodation space and the main body internal space, a door side pressure-contact portion in which an opening portion at one end side of the hole portion is closed as being pressure-contacted with a door face when the passage opening/closing door is closed while the opening portion at the one end side is placed in the main body internal space, and a container side pressure-contact portion which seals the container opening portion as being sandwiched and pressure-contacted by the fragrance retention container and the main body while the opening portion of the other end side of the hole portion is placed between the fragrance retention container and the main body or in the accommodation space; and the door side pressure-contact portion and the container side pressure-contact portion are integrally formed.

17. The sealing component for a vehicle-use fragrance device according to claim 16, wherein the container side pressure-contact portion seals the main body opening portion.

18. The sealing component for a vehicle-use fragrance device according to claim 16, wherein a center portion of a section of the door side pressure-contact portion placed in the main body internal space has a larger outer diameter than the diameter of the main body opening portion.

19. The sealing component for a vehicle-use fragrance device according to claim 16, further comprising plural through pathways respectively constituted with the hole portion, the door side pressure-contact portion and the container side pressure-contact portion, wherein the whole is integrally formed.

20. The sealing component for a vehicle-use fragrance device according to claim 16, wherein the sealing component is formed of elastomer.

21. The sealing component for a vehicle-use fragrance device according to claim 20, wherein the sealing component is integrally formed with the fragrance retention container.

22. The sealing component for a vehicle-use fragrance device according to claim 16, wherein the sealing component is formed of butyl rubber.

23. The sealing component for a vehicle-use fragrance device according to claim 16, wherein the sealing component is formed of silicone series rubber.

* * * * *